United States Patent
Yang et al.

(10) Patent No.: US 10,322,140 B2
(45) Date of Patent: Jun. 18, 2019

(54) PREPARATION AND USE OF 7A-HETEROCYCLE SUBSTITUTED-6,6-DIFLUORO BICYCLIC HIMBACINE DERIVATIVES AS PAR-1 RECEPTOR ANTAGONISTS

(71) Applicant: Merck Sharp & Dohme Corp., Rahway, NJ (US)

(72) Inventors: Zhiqiang Yang, Westfield, NJ (US); Guizhen Dong, Dayton, NJ (US); Milana Maletic, Summit, NJ (US)

(73) Assignee: Merck Sharp & Dohme Corp.

( * ) Notice: Subject to any disclaimer, the term of this patent is extended or adjusted under 35 U.S.C. 154(b) by 69 days.

(21) Appl. No.: 15/715,446

(22) Filed: Sep. 26, 2017

(65) Prior Publication Data
US 2018/0015106 A1    Jan. 18, 2018

Related U.S. Application Data

(63) Continuation of application No. 14/912,212, filed as application No. PCT/US2014/051403 on Aug. 18, 2014, now abandoned.
(Continued)

(51) Int. Cl.
*C07D 405/14* (2006.01)
*C07D 413/14* (2006.01)
(Continued)

(52) U.S. Cl.
CPC .......... *A61K 31/60* (2013.01); *A61K 31/4155* (2013.01); *A61K 31/4245* (2013.01);
(Continued)

(58) Field of Classification Search
CPC .............................. C07D 405/14; C07D 413/14
See application file for complete search history.

(56) References Cited

U.S. PATENT DOCUMENTS

| | | |
|---|---|---|
| 6,326,380 B1 | 12/2001 | Chackalamannil et al. |
| 7,776,889 B2 | 8/2010 | Chackalamannil et al. |

(Continued)

FOREIGN PATENT DOCUMENTS

| | | |
|---|---|---|
| KR | 20120111887 | 10/2012 |
| WO | WO2011162562 | 12/2011 |

(Continued)

OTHER PUBLICATIONS

Extended European Search Report for 14838369.8, dated Feb. 7, 2017, 7 pages.
(Continued)

*Primary Examiner* — Jeffrey S Lundgren
*Assistant Examiner* — Meghan Finn
(74) *Attorney, Agent, or Firm* — Catherine D. Fitch; Sarah Hooson

(57) ABSTRACT

The present invention relates to bicyclic himbacine derivatives of the formula

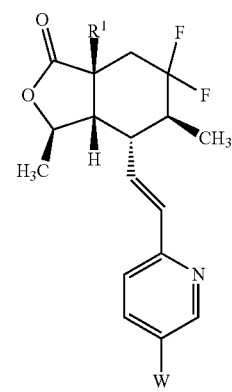

I or a pharmaceutically acceptable salt thereof wherein:
$R^1$ is

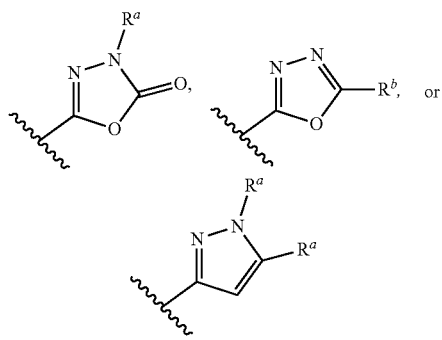

W is

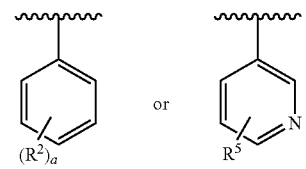

and the remaining variables are described herein. The compounds of the invention are effective inhibitors of the PAR-1 receptor. The inventive compounds may be used for the treatment or prophylaxis of disease states such as ASC, secondary prevention of myocardial infarction or stroke, or PAD.

13 Claims, No Drawings

Related U.S. Application Data

(60) Provisional application No. 61/868,597, filed on Aug. 22, 2013.

(51) Int. Cl.
*A61K 31/60* (2006.01)
*A61K 31/4439* (2006.01)
*A61K 45/06* (2006.01)
*A61K 31/4155* (2006.01)
*A61K 31/4245* (2006.01)
*A61K 31/4365* (2006.01)
*A61K 31/444* (2006.01)

(52) U.S. Cl.
CPC ........ *A61K 31/4365* (2013.01); *A61K 31/444* (2013.01); *A61K 31/4439* (2013.01); *A61K 45/06* (2013.01); *C07D 405/14* (2013.01); *C07D 413/14* (2013.01)

(56) References Cited

U.S. PATENT DOCUMENTS

| | | | |
|---|---|---|---|
| 8,871,798 | B2 | 10/2014 | Schoenafinger et al. |
| 9,340,530 | B2 | 5/2016 | Mandal et al. |
| 2002/0026050 | A1 | 2/2002 | Chackalamannil et al. |
| 2003/0216437 | A1 | 11/2003 | Chackalamannil et al. |
| 2004/0006105 | A1 | 1/2004 | Chackalamannil et al. |
| 2004/0152736 | A1 | 8/2004 | Chackalamannil et al. |
| 2005/0267155 | A1 | 12/2005 | Chelliah et al. |
| 2006/0079684 | A1 | 4/2006 | Chackalamannil et al. |
| 2006/0106050 | A1 | 5/2006 | Chakalamannil et al. |
| 2007/0149518 | A1 | 6/2007 | Chackalamannil et al. |
| 2008/0090830 | A1 | 4/2008 | Chackalamannil et al. |
| 2011/0301112 | A1 | 12/2011 | Xia et al. |
| 2012/0157403 | A1 | 6/2012 | Chackalamannil et al. |
| 2012/0184504 | A1 | 7/2012 | Strony et al. |

FOREIGN PATENT DOCUMENTS

| | | |
|---|---|---|
| WO | 2013134012 A1 | 9/2013 |
| WO | WO2015026686 A1 | 2/2015 |
| WO | WO2015026693 A1 | 2/2015 |

OTHER PUBLICATIONS

International Search Report and Written Opinion for PCT/US2014/051403 dated Nov. 28, 2014; 10 pages.
U.S. Appl. No. 14/912,212, filed Feb. 16, 2016.

PREPARATION AND USE OF 7A-HETEROCYCLE SUBSTITUTED-6,6-DIFLUORO BICYCLIC HIMBACINE DERIVATIVES AS PAR-1 RECEPTOR ANTAGONISTS

CROSS REFERENCE TO RELATED APPLICATIONS

This application is a continuation of U.S. application Ser. No. 14/912,212 filed on Feb. 16, 2016, which is a U.S. National Phase application under 35 U.S.C. § 371 of PCT Application No. PCT/US2014/051403 filed Aug. 18, 2014, which claims priority from U.S. Provisional Application Ser. No. 61/868,597, filed Aug, 22, 2013.

FIELD OF THE INVENTION

The present invention relates to 7a-heterocycle substituted 6,6-difluro bicyclic himbacine derivatives, which are useful as protease activated receptor-1 (PAR-1) antagonists and might be expected to be cannabinoid ($CB_2$) receptor inhibitors. PAR-1 receptors are also known in the art as thrombin receptor antagonists (TRA). The inventive compounds have utility in treating disease states such as acute coronary syndrome (ACS) (unstable angina, non-ST-segment elevation [NSTE] myocardial infarction [MI], and ST segment-elevation myocardial infarction [STEMI]), secondary prevention of myocardial infarction or thrombotic stroke (secondary prevention) or peripheral artery disease (PAD), which is also know in the art as peripheral vascular disease. The present invention also relates to pharmaceutical compositions comprising the inventive compounds as well as processes for their preparation.

BACKGROUND OF THE INVENTION

Thrombin is known to have a variety of activities in different cell types. PAR-1 receptors are known to be present in such cell types as human platelets, vascular smooth muscle cells, endothelial cells and fibroblasts. The art indicates that PAR-1 receptor antagonists would be expected to be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, the art suggests that a selective $CB_2$ receptor binding agent might be expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635; M. Bensaid, *Molecular Pharmacology*, 63 (4), (2003), 908).

Himbacine, a piperidine alkaloid of the formula

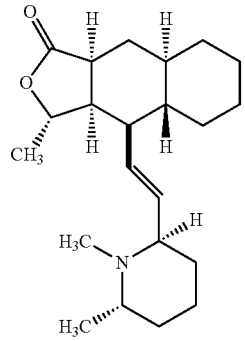 [SMILES: C[C@@H]1OC(=O)[C@H]2C[C@H]3CCCC[C@@H]3[C@@H](/C=C/[C@H]3CCC[C@H](C)N3C)[C@@H]12]

has been identified as a muscarinic receptor antagonist. The total synthesis of (+)-himbacine is disclosed in Chackalamannil et al., *J. Am. Chem. Soc.*, 118 (1996), p. 9812-9813.

Substituted bi- and tricyclic thrombin receptors antagonists are known in the art to treat thrombin receptor mediated disorders such as thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction, as well as $CB_2$ receptor mediated disorders. U.S. Pat. No. 6,645,987 and U.S. Pat. No. 6,894,065 disclose PAR-1 receptor antagonists of the structure:

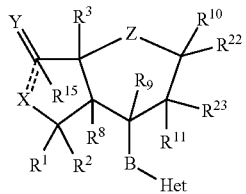

where $R^{10}$ may be groups such as H, alkyl, haloalkyl, hydroxyl, etc. and $R^{22}$ may be groups such as H, optionally substituted alkyl, hydroxyl, etc. Other known substituted thrombin receptor antagonists are disclosed in WO2001/96330, U.S. Pat. Nos. 6,063,847, 6,326,380, 7,037,920, 7,488,742, 7,713,999, 7,442,712, 7,488,752, 7,776,889, 7,888,369, 8,003,803 and U.S. Pat. No. 8,022,088. US 2008/0090830 and Chackalamannil et al., *J. Med. Chem.*, 49 (2006), p. 5389. A PAR-1 receptor antagonist that exhibits good thrombin receptor antagonist activity (potency) and selectivity is vorapaxar (Merck & Co., Inc.), which has the following structure:

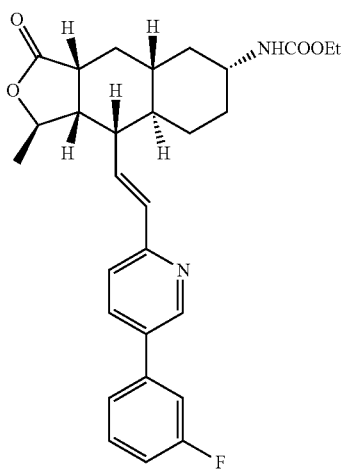

This compound underwent clinical trials and is disclosed in U.S. Pat. No. 7,304,048. A crystalline form of the bisulfate salt of vorapaxar is disclosed in U.S. Pat. No. 7,235,567.

WO2011/162,562 to LG Life Sciences LTD. describes a series of [6+5] fused bicycle derivatives of the general structure:

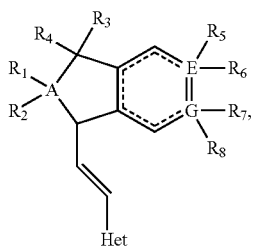

where $R_5$ and $R_6$ are inter alia both fluoro groups, as inhibitors of the PAR-1 receptor. The compounds are taught to be useful in the treatment and prevention of thrombus, platelet aggregation, atherosclerosis, restenosis, blood coagulation, hypertension, arrhythmia, angina pectoris, heart failure, inflammation and cancer when used alone or with other cardiovascular agents.

WO2011/28420 and WO2011/28421, both to Sanofi-Aventis, disclose compounds that are reported to be PAR-1 receptor antagonists. The compounds disclosed in WO2011/28420 are pyridyl-vinyl pyrazoloquinolines derivatives and have the following general structure:

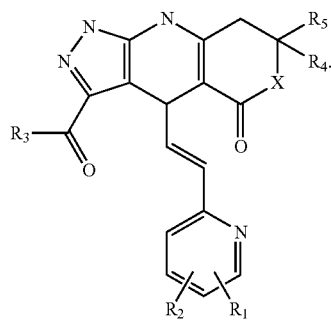

WO2011/28421 discloses tryicyclic pyridyl-vinyl-pyrrole derivatives of the following general structure:

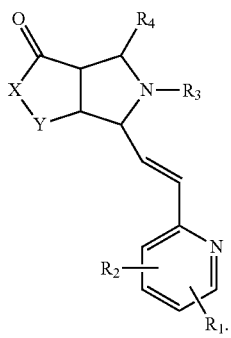

PCT/US13/027383 to Merck Sharpe & Dohme Corp. discloses bicyclic himbacine derivatives of the following general structure

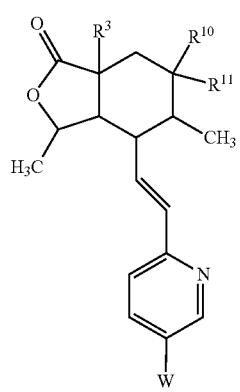

where $R^{10}$ and $R^{11}$ may both be fluoro groups. These compounds are PAR-1 receptor antagonists.

Applicants discovered in accordance with the present invention that the inventive compounds act as inhibitors of PAR-1 receptor and, based upon their structure, might also act as inhibitors of the $CB_2$ receptor. Therefore, the inventive compounds might be expected to be useful in treating disease states associated with the inhibition of these receptors.

There is a need for new compounds, formulations, treatment and therapies to treat diseases associated with the PAR-1 and $CB_2$ receptors. Moreover, there is a need to develop therapeutics that exhibit improved therapeutic profiles; for example, desirable half-life or reduced unintended effects, such as reduced drug-drug interactions (DDIs). DDIs are potentially undesirable as they can reduce the therapeutic effectiveness of an agent or increase the incidence of unintended effects associated with the drug. It is, therefore, an object of this invention to provide compounds useful in the treatment, prevention or amelioration of such diseases or disorders with improved therapeutic profiles. These and other objectives will become evident from the following description.

SUMMARY OF THE INVENTION

In its many embodiments, the present invention provides for a novel group of bicyclic himbacine derivatives, which are PAR-1 receptor antagonists, or metabolites, stereoisomers, salts, solvates or polymorphs thereof, processes of preparing such compounds, pharmaceutical compositions comprising one or more such compounds, processes of preparing pharmaceutical compositions comprising one or more such compounds and potentially methods of treatment, inhibition or amelioration of one or more disease states associated with the PAR-1 receptor by administering an effective amount at least one of the inventive bicyclic himbacine derivatives to a patient in need thereof.

In one aspect, the present application discloses a compound or a pharmaceutically acceptable salt, metabolite, solvate, prodrug or polymorph of said compound, said compound or pharmaceutically acceptable salt thereof having the general structure shown in Formula I

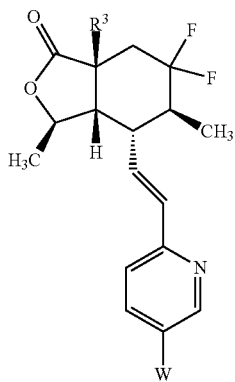

I wherein:
$R^1$ is

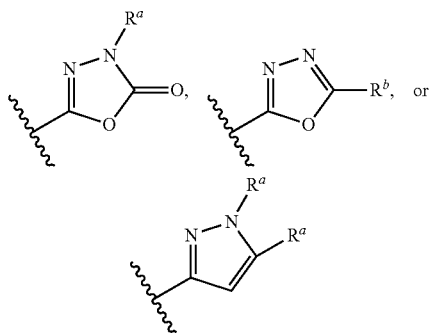

W is

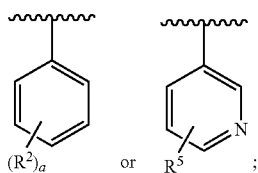

$R^a$ is independently H or $C_1$-$C_4$ alkyl;
$R^b$ is H; $C_1$-$C_4$ alkyl; cycloalkyl (e.g., cyclopropyl); —N($R^3$)($R^4$); or phenyl, which is independently optionally substituted once or twice by alkyl, haloalkyl, —OH, or alkoxy;
$R^2$ is independently halo; —CN; alkyl; or haloalkyl;
$R^3$ is H or alkyl;
$R^4$ is H or alkyl;
$R^5$ is H, alkyl or —CN; and
a is 0, 1 or 2.

Another aspect of the present invention is pharmaceutical compositions comprising a therapeutically effective amount of at least one compound of Formula I or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, at least one additional cardiovascular agent and a pharmaceutically acceptable carrier.

Another aspect of the present invention is the possible prevention of one or more disease state associated with inhibiting the PAR-1 receptor by administering an effective amount of a compound of Formula I or a pharmaceutically acceptable salt thereof to a patient in need thereof.

Another aspect of the present invention is a method of inhibiting platelet aggregation comprising administering to a mammal an effective amount of a compound of Formula I or a pharmaceutically acceptable salt thereof.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a cardiovascular agent.

The compounds of the present invention can potentially be useful in the treatment, amelioration or prevention of one or more conditions associated with inhibiting the PAR-1 receptor by administering at least one compound of Formula I or a pharmaceutically acceptable salt thereof to a mammal in need of such treatment. Conditions that could potentially be treated or prevented by inhibiting the PAR-1 receptor include thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction.

Another embodiment is the possible treatment, amelioration or prevention of ACS, secondary prevention of myocardial infarction or stroke, urgent coronary revascularization, or PAD by administering at least one compound of Formula I or a pharmaceutically acceptable salt thereof to a mammal in need of such treatment.

Another embodiment of this invention is in the possible treatment, amelioration or prevention of one or more conditions associated with cardiopulmonary bypass surgery (CPB) by administering effective amount of at least one compound of Formula I or a pharmaceutically acceptable salt thereof to a subject of said CPB surgery. CPB surgery includes coronary artery bypass surgery (CABG), cardiac valve repair and replacement surgery, pericardial and aortic repair surgeries. The conditions associated with CABG include bleeding, thrombotic vascular events (such as thrombosis or restenosis), vein graft failure, artery graft failure, atherosclerosis, angina pectoris, myocardial ischemia, acute coronary syndrome, myocardial infarction, heart failure, arrhythmia, hypertension, transient ischemic attack, cerebral function impairment, thromboembolic stroke, cerebral ischemia, cerebral infarction, thrombophlebitis, deep vein thrombosis and PAD.

Another embodiment of the present invention is the possible use of a compound of Formula I or a pharmaceutically acceptable salt thereof for the manufacture of a medicament for the treatment, amelioration or prevention of one or more conditions associated with inhibiting the PAR-1 receptor in a patient.

DETAILED DESCRIPTION

In an embodiment, the present invention provides compounds represented by structural Formula I, or pharmaceutically acceptable salt thereof, wherein the various moieties are as described as above.

Another embodiment is the following compounds:
2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl) benzonitrile (1);
2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl)-6-methylbenzonitrile (2);
2-(6-((E)-2-((3R,3aS,4R,5S,7aR)-7a-(5-amino-1,3,4-oxadiazol-2-yl)-6,6-difluoro-3,5-dimethyl-1-oxooctahydroiso benzofuran-4-yl)vinyl)pyridin-3-yl)-6-methylbenzonitrile (3);
2-(6-((E)-2-((3R,3aS,4R,5S,7aR)-7a-(5-amino-1,3,4-oxadiazol-2-yl)-6,6-difluoro-3,5-dimethyl-1-oxooctahydroiso benzofuran-4-yl)vinyl)pyridin-3-yl)benzonitrile (4);
2-(6-((E)-2-((3R,3aS,4R,5S,7aR)-6,6-difluoro-3,5-dimethyl-7a-(5-methyl-1,3,4-oxadiazol-2-yl)-1-oxooctahydroisobenzofuran-4-yl)vinyl)pyridin-3-yl)-6-methylbenzonitrile (5);
2-(6-((E)-2-((3R,3aS,4R,5S,7aR)-7a-(5-cyclopropyl-1,3,4-oxadiazol-2-yl)-6,6-difluoro-3,5-dimethyl-1-oxooctahydroisobenzofuran-4-yl)vinyl)pyridin-3-yl)-6-methylbenzonitrile (6);
2-(6-((E)-2-((3R,3aS,4R,5S,7aR)-6,6-difluoro-3,5-dimethyl-1-oxo-7a-(5-phenyl-1,3,4-oxadiazol-2-yl) octahydroisobenzofuran-4-yl)vinyl)pyridin-3-yl)-6-ethylbenzonitrile (7);
5-((1R,3aR,6S,7R,7aS)-5, 5-difluoro-7-((E)-2-(5-(3-fluorophenyl)pyridin-2-yl)vinyl)-1,6-dimethyl-3-oxooctahydroisobenzofuran-3a-yl)-1,3,4-oxadiazol-2(3H)-one (8);
2-(6-((E)-2-((3R,3aS,4R,5S,7aR)-7a-(5-(tert-butyl)-1H-pyrazol-3-yl)-6,6-difluoro-3,5-dimethyl-1-oxooctahydroisobenzofuran-4-yl)vinyl)pyridin-3-yl)benzonitrile (9);
2-(6-((E)-2-((3R,3aS,4R,5S,7aR)-7a-(5-(tert-butyl)-1-methyl-1H-pyrazol-3-yl)-6,6-difluoro-3,5-dimethyl-1-oxooctahydroisobenzofuran-4-yl)vinyl)pyridin-3-yl) benzonitrile (10);
2-(6-((E)-2-((3R,3aS,4R,5S,7aR)-7a-(1,5-dimethyl-1H-pyrazol-3-yl)-6,6-difluoro-3,5-dimethyl-1-oxooctahydroiso benzofuran-4-yl)vinyl)pyridin-3-yl)benzonitrile (11);
6'-((E)-2-((3R,3aS,4R,5S,7aR)-6,6-difluoro-3,5-dimethyl-1-oxo-7a-(1H-pyrazol-3-yl)octahydroisobenzofuran-4-yl)vinyl)-[3,3'-bipyridine]-2-carbonitrile (13) or a pharmaceutically acceptable salt thereof.

Another embodiment of the present invention is the following compounds or a pharmaceutically acceptable salt thereof wherein $R^1$ is

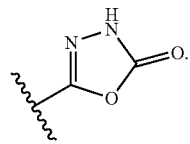 [SMILES: *c1n[nH]c(=O)o1]

Another embodiment of the present invention is the following compounds or a pharmaceutically acceptable salt thereof wherein $R^1$ is

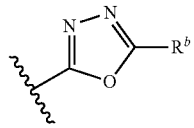

and $R^b$ is —NH$_2$, alkyl (e.g., methyl or ethyl), cyclopropyl or phenyl.

Another embodiment of the present invention is the following compounds or a pharmaceutically acceptable salt thereof wherein $R^1$ is

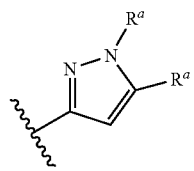

and $R^a$ independently is H or alkyl (e.g., methyl, ethyl, n-propyl, n-butyl, iso-butyl or tert-butyl).

Another embodiment is a compound of Formula I or a pharmaceutically acceptable salt thereof wherein W is

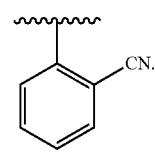

Another embodiment is a compound of Formula I or a pharmaceutically acceptable salt thereof wherein W is

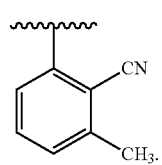

Another embodiment is a compound of Formula I or a pharmaceutically acceptable salt thereof wherein W is

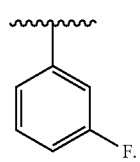

Another embodiment is a compound of Formula I or a pharmaceutically acceptable salt thereof wherein W is

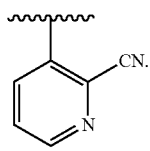 [SMILES: *c1cccnc1C#N]

As used above, and throughout this disclosure, the following terms, unless otherwise indicated, shall be understood to have the following meanings:

"Patient" or "subject" includes both humans and animals.

"Mammal" means humans and other mammalian animals.

"Alkyl" means an aliphatic hydrocarbon group which may be straight or branched and comprising about 1 to about 20 carbon or about 1 to 12 atoms in the chain. "Lower alkyl" means a group having about 1 to about 6 carbon atoms in the chain which may be straight or branched. Non-limiting examples of "alkyl" include those have about 1 to 4 carbon atoms in the chain, such as methyl, ethyl, n-propyl, isopropyl, n-butyl, iso-butyl, and tert-butyl. Branched means that one or more lower alkyl groups such as methyl, ethyl or propyl, are attached to a linear alkyl chain.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Halo" refers to fluorine, chlorine, bromine or iodine radicals. Non-limiting examples include fluoro, chloro or bromo, or fluoro and chloro.

"Halogen" means fluorine, chlorine, bromine, or iodine. Non-limiting examples include fluorine or chlorine.

"Haloalkyl" means a halo-alkyl-group in which the alkyl group is as previously described. The bond to the parent moiety is through the alkyl. Non-limiting examples of suitable haloalkyl groups include fluoromethyl, difluoromethyl, —$CH_2CF_3$, —$CH_2CHF_2$ or —$CH_2CH_2F$.

"Cycloalkyl" is a cyclized alkyl ring having 3-12 or 3-6 carbon atoms. Examples of cycloalkyl include cyclopropyl, cyclobutyl, cyclopentyl and cyclohexyl.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

"Effective amount" or "therapeutically effective amount" is meant to describe an amount of compound or a composition of the present invention effective as PAR-1 or thrombin receptor antagonists, thereby producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In this application, unless otherwise indicated, whenever there is a structural formula provided, such as those of Formula I, this formula is intended to encompass all forms of a compound such as, for example, any solvates, hydrates, stereoisomers, tautomers, co-crystals, polymorphs etc.

Compounds of Formula I, and salts, solvates, co-crystals and prodrugs thereof, may exist in their tautomeric form (for example, as an amide or imino ether). All such tautomeric forms are contemplated herein as part of the present invention.

Prodrugs, solvates and co-crystals of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

A co-crystal is a crystalline superstructure formed by combining an active pharmaceutical intermediate with an inert molecule and provides crystallinity to the combined form. Co-crystals are often made between a dicarboxlyic acid such as fumaric acid, succinic acid etc. and a basic amine, such as the one represented by a compound of this invention in different proportions depending on the nature of the co-crystal. (Remenar, J. F. et. al. *J Am. Chem. Soc.* 2003, 125, 8456).

All stereoisomers (for example, geometric isomers, optical isomers and the like) of the present compounds (including those of the salts, solvates, co-crystals and prodrugs of the compounds as well as the salts and solvates, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically-labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

As discussed above, the compounds of Formula I may be used to treat, ameliorate or prevent conditions associated with inhibiting the PAR-1 receptor. In addition to the conditions mentioned above, other conditions could include migraine, erectile dysfunction, rheumatoid arthritis, rheumatism, astrogliosis, a fibrotic disorder of the liver, kidney, lung or intestinal tract, systemic lupus erythematosus, multiple sclerosis, osteoporosis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy, malignant tumors, neurodegenerative and/or neurotoxic diseases, conditions or injuries, Alzheimer's disease, an inflammatory disease or condition, asthma, glaucoma, macular degeneration, psoriasis, endothelial dysfunction disorders of the liver, kidney or lung, inflammatory disorders of the lungs and gastrointestinal tract, respiratory tract disease or condition, radiation fibrosis, endothelial dysfunction, periodontal diseases or wounds, or a spinal cord injury, or a symptom or result thereof, viral infections, including infections from human respiratory syncytial virus (hRSV), human metapneumovirus (hMPV) and influenza virus type A, as well as other disorders in which thrombin and its receptor play a pathological role.

In addition to their PAR-1 receptor antagonist properties, the compounds of Formula I or the pharmaceutically acceptable salts might be expected to be used to treat, ameliorate or prevent one or more conditions associated with inhibiting the $CB_2$ receptor by administering at least one compound of Formula I or a pharmaceutically acceptable salt thereof to a mammal in need of such treatment. Conditions might include, for example, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

In another embodiment, compounds of the present invention might be expected to be useful in a method for treating, ameliorating or preventing radiation- and/or chemical-induced toxicity in non-malignant tissue in a patient comprising administering a therapeutically effective amount of at least one compound of Formula I or a pharmaceutically acceptable salt thereof. In particular, the radiation- and/or chemical-induced toxicity is one or more of intestinal fibrosis, pneumonitis, and mucositis. In one embodiment, the radiation- and/or chemical-induced toxicity is intestinal fibrosis. In another embodiment, the radiation- and/or chemical-induced toxicity is oral mucositis. In yet another embodiment, the radiation- and/or chemical-induced toxicity is intestinal mucositis, intestinal fibrosis, intestinal radiation syndrome, or pathophysiological manifestations of intestinal radiation exposure.

The present invention might also be expected to provides for methods for reducing structural radiation injury in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing inflammation in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for adverse tissue remodeling in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing fibroproliferative tissue effects in a patient that will be exposed, is concurrently exposed, or was exposed to radiation and/or chemical toxicity, comprising administering a therapeutically effective amount of at least one compound of Formula I or a pharmaceutically acceptable salt thereof.

The present invention might also be expected to provide for methods useful for treating a cell proliferative disorder in a patient suffering therefrom comprising administering a therapeutically effective amount of at least one compound of Formula I or a pharmaceutically acceptable salt thereof. In one embodiment, the cell proliferative disorder is pancreatic cancer, glioma, ovarian cancer, colorectal and/or colon cancer, breast cancer, prostate cancer, thyroid cancer, lung cancer, melanoma, or stomach cancer. In one embodiment, the glioma is an anaplastic astrocytoma. In another embodiment, the glioma is a glioblastoma multiforme.

As used above, the term "inflammatory disease or condition" includes irritable bowel syndrome, Crohn's disease, nephritis or a radiation- or chemotherapy-induced proliferative or inflammatory disorder of the gastrointestinal tract, lung, urinary bladder, gastrointestinal tract or other organ. The term respiratory tract disease or condition includes reversible airway obstruction, asthma, chronic asthma, bronchitis or chronic airways disease. "Cancer" includes renal cell carcinoma or an angiogenesis related disorder. "Neurodegenerative disease" includes Parkinson's disease, amyotropic lateral sclerosis, Alzheimer's disease, Huntington's disease or Wilson's disease.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically acceptable carrier. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The amount and frequency of administration of the compound of this invention and/or their pharmaceutically acceptable salts will be regulated according to the judgment of the attending clinician considering such factors as age, condition and size of the patient as well as the severity of the symptoms being treated.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" are used herein to refer to administering a compound before the onset of clinical symptoms.

The compounds of this invention may also be useful in combination (administered together or sequentially) with one or more therapeutic agents, such as, for example, another cardiovascular agent. Cardiovascular agents that could be used in combination with the compounds for Formula I or their pharmaceutically acceptable salts include drugs that have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartan, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Other possible combinations might include lipid lowering agents (e.g., simvastatin, lovastatin, pravastatin, atorvastatin rosuvastatin, pitavastatin, ezetimibe); niacin in immediate-release or controlled release forms or niacin in combination with a DP antagonist, such as laropiprant and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone statins, e.g., simvastatin, atorvastatin and rosovastatin), PCSK9 inhibitors, e.g. antibodies—REGN727, AMG-145, RN316, RG7652; and small molecule inhibitors and CETP inhibitors, e.g., anacetrapib, evacetrapib, etc. Other possible combinations include AMPK agonists (e.g., ETC-1002); glucagon receptor antagonists; Lp-PLA2 inhibitors (e.g., darapladib) and anti-IL-1beta antibodies (canakinumab).

The dosage of the cardiovascular agent can be determined from published material, and may range from 1 to 1000 mg per dose.

An embodiment of this invention is combinations comprising an effective amount of a compound of Formula I or a pharmaceutically acceptable salt thereof and an ADP antagonist and/or cyclooxygenase inhibitor.

Non-limiting combinations comprise an effective amount of a compound according to Formula I or a pharmaceutically acceptable salt thereof and aspirin, ticagrelor, cangrelor, clopidogrel (either as a free base or as a pharmaceutically acceptable salt, such as its bisulfate salt), prasugrel, ticlopidine or fragmin.

Other therapeutic agents could include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases and wounds. Further examples of therapeutically effective agents which may be administered in combination with a compound of Formula I or a pharmaceutically acceptable salt thereof include resistance factors for tumor cells towards chemotherapy and proliferation inhibitors of smooth muscle cells, endothelial cells, fibroblasts, kidney cells, osteosarcoma cells, muscle cells, cancer cells and/or glial cells.

For treating and/or preventing radiation- and/or chemical-induced toxicity in non-malignant tissue, the present invention includes administering to a patient in need of such treatment an effective amount of a combination of one or more compounds of formula I and one or more radiation-response modifiers selected from the group consisting of Kepivance™ (palifermin), L-glutamine, teduglutide, sucralfate mouth rinses, iseganan, lactoferrin, mesna and trefoil factor.

For treating a cell proliferative disorder the present invention includes administering to a patient in need of such treatment an effective amount of a combination of one or more compounds of Formula I or a pharmaceutically acceptable salt thereof and another antineoplastic agent. In one embodiment, the other antineoplastic agent is temozolomide and the cell proliferative disorder is glioma. In another embodiment, the other antineoplastic agent is interferon and the cell proliferative disorder is melanoma. In one embodiment, the other antineoplastic agent is PEG-Intron (peginterferon alpha-2b) and the cell proliferative disorder is melanoma.

Pharmaceutical compositions comprising a therapeutically effective amount of a combination of at least one compound of Formula I or a pharmaceutically acceptable salt thereof and a radiation-response modifier in a pharmaceutically acceptable carrier are also provided.

Pharmaceutical compositions comprising a therapeutically effective amount of a combination of at least one compound of Formula I or a pharmaceutically acceptable salt thereof and an antineoplastic agent in a pharmaceutically acceptable carrier are also provided.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

Moreover, one skilled in the art would have resources such as Chemical Abstracts or Beilstein at his or her disposal to assist in preparing a specific compound.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, 1H spectra were obtained, for example, on either a Varian Inova (400 or 500 mHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed, for example, using an Agilent 1100 series or Applied Biosystems® API-100 mass spectrometer and C18 column, 5-95% $CH_3CN$—$H_2O$ (with 0.05% TFA) gradient. The observed parent ion is given Throughout the synthetic schemes, abbreviations are used with the following meaning unless otherwise indicated:
ACN or MeCN=acetonitrile; $Ac_2O$=acetic anhydride; Aq.=aqueous; t-Butyl=tert-butyl; t-BuOH=tert-butyl alcohol; cat.=catalyst; DBU=1,8-Diazabicyclo[5.4.0]undec-7-ene; DCC=N,N'-bicyclohexylcarbodiimide; DCM=dichloromethane; DAST=diethylaminosulfur trifluoride; DMAC=N,N-dimethylacetamide; DMAP=4-dimethylamino pyridine; DMEM=Dulbecco's modified eagle medium, DMF=dimethylformamide; DMP=Dess-Martin periodinane; DMSO=dimethylsulfoxide; DIEA=N,N-Diisopropylethylamine or Hünig's base; Et=ethyl; EtOH=ethanol; EtOAc=ethyl acetate; g=gas HATU=O-(7-azabenzotriazol-1-yl)-N,N,N',N'-tetramethyluronium hexafluorophosphate; HEPES=(4-(2-hydroxyethyl)-1-piperazineethanesulfonic acid); HPLC=high pressure liquid chromatography; HOAc=acetic acid; LCMS=liquid chromatorgraphy-mass spectrometry; KHMDS=Potassium bis(trimethylsilyl)amide; LiHMDS=lithium bis(trimethylsilyl)amide; Me=methyl; MeOH=methanol; MeI=methyl iodide; mmol=millimoles MPLC=medium pressure liquid chromatography; Ms=mesylate; MS ESI=electrospray ionixation mass spectrometry; MTBE=methyl tert-butyl ether; NMM=M-methylmorpholine; NMP=N-methyl-2-pyrrolidone; Ph=phenyl; piv-cl=pivaloyl chloride; i-Pr=iso-propyl; RT or rt=room temperature TEA=triethanolamine; TFA=trifluoroacetic acid; THF=tetrahydrofuran; TLC=thin layer chromatography.

INTERMEDIATE SYNTHESES

Intermediate compounds of the present invention can be synthesized according to the schemes and procedures outlined below. Since the schemes are an illustration, the invention should not be construed as being limited by the chemical reactions and conditions expressed. The preparation of the various starting materials used in the schemes is well within the ordinary skill level of a practitioner of this art. Unless otherwise indicated, the definition for a variable is the same as that provided in Formula I.

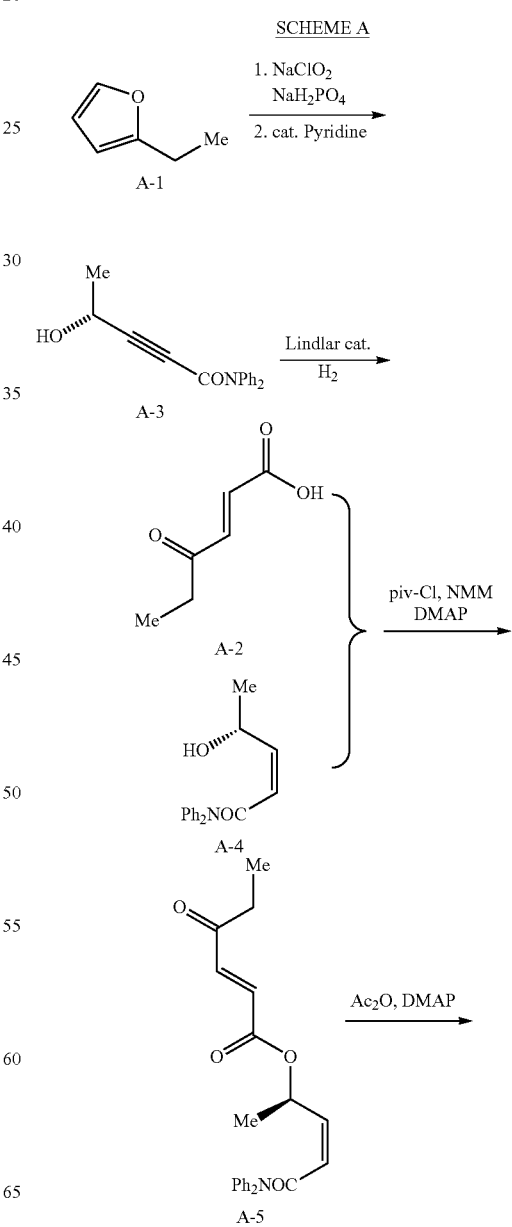

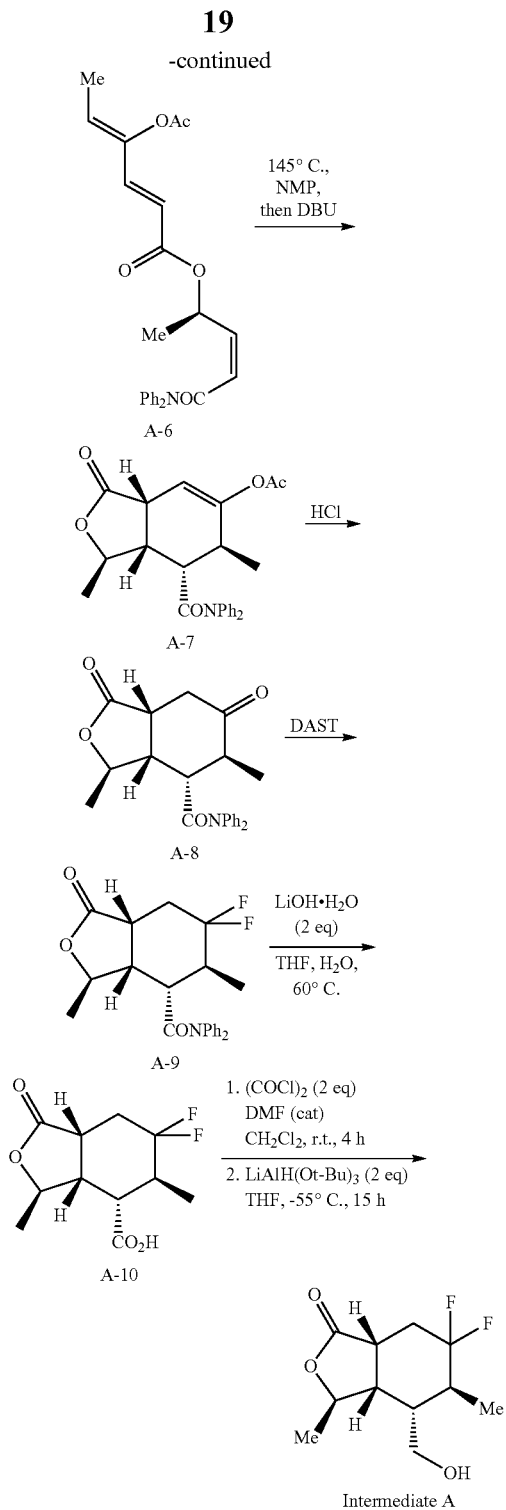

stage for an intramolecular Diels-Alder reaction to form lactone (A-7). Hydrolysis and subsequent reaction of ketone (A-8) with DAST provided the C6-difluoro lactone (A-9). Saponification of the amide provided carboxylic acid (A-10), which was then chemoselectively reduced via a two-step protocol to yield Intermediate A.

Intermediate A

Step 1: 5-ethyl-5-hydroxyfuran-2(5H)-one: $NaH_2PO_4$ (243 g, 3.12 mol) was added to a solution of 2-ethylfuran (100 g, 1.04 mol) in t-BuOH (1.0 L) and $H_2O$ (200 mL) at room temperature. After 30 min, $NaClO_2$ (312 g, 3.12 mol) was added portionwise. The temperature was controlled between 10-30° C. After the addition, the reaction was stirred for another 2 h until the reaction goes to completion. The reaction solution was purged with $N_2$ overnight until it turned to white. The precipitate was filtered and t-BuOH was removed under vacuo. The reaction was extracted with $CH_2Cl_2$ and dried with anhydrous $Na_2SO_4$. After combining all thirteen reactions and concentration, the title compound was obtained and was used directly for the next step without further purification.

Step 2: (E)-4-oxohex-2-enoic acid: To a solution of 5-ethyl-5-hydroxyfuran-2(5H)-one (130 g, 1.02 mol) in THF (645 mL) was added acetone (520 mL), water (130 mL), pyridine (8.1 mL, 0.1 mol) at room temperature. The reaction was stirred overnight. TLC (petroleum ether/ethyl acetate, 3:1) showed the reaction was completed. The mixture was concentrated under vacuo. The residue was treated with 10% $K_2CO_3$ to pH >10 at 0° C. and extracted with ethyl acetate (500 mL×3). The aqueous layer was acidified with concentrated HCl at 0° C. to pH <2. After extraction with ethyl acetate (500 mL×6) and washing with brine, the organic layer was dried with anhydrous $Na_2SO_4$ and concentrated to give the title compound. It was washed with methyl tert-butyl ether to provide the title compound. $^1$H NMR (400 MHz, $CDCl_3$) δ 7.12 (d, 1H, J=16.0 Hz), 6.66 (d, 1H, J=15.6 Hz), 2.68 (q, 2H, J=7.2 Hz), 1.13 (q, 2H, J=7.2 Hz).

Step 3: (R,Z)-4-hydroxy-N,N-diphenylpent-2-enamide: To a solution of (R)-4-hydroxy-N,N-diphenylpent-2-ynamide (200 g, 0.75 mol) and Lindlar catalyst (13.6 g, 7.5 mmol) in $CH_3OH$ (2 L) was added quinoline (21.6 mL, 182 mmol) at room temperature. The reaction was evacuated and recharged with a balloon of $H_2$. After stirring at room temperature for 1 h, TLC (petroleum ether/ethyl acetate, 3:1) showed the reaction was complete. Solvent was removed under reduced pressure at 35° C. THF (1 L) was added which was followed by the addition of petroleum ether (1 L). After removing half amount of the solvent, petroleum ether (1 L) was added. A precipitate formed during concentration, which was filtered and washed with methyl tert-butyl ether to afford the title compound. The combined filtrate residues were purified by silica gel column chromatography (petroleum ether:ethyl acetate, Intermediate A can be prepared from commercially available and known starting materials according to Scheme A. 2-Ethylfuran (A-1) was oxidized to the corresponding hydroxyfuranone, which under the action of base is opened to carboxylic acid (A-2). Alkynylalcohol (A-3) was reduced to the corresponding cis-alkene (A-4) using Lindlar's catalyst under an atmosphere of hydrogen gas. DCC-mediated coupling of prepared intermediates (A-2) and (A-4) provided the complete carbon framework for intermediate A in compound (A-5). Formation of the enol acetate (A-6) set the 5:1) to yield another batch of (R,Z)-4-hydroxy-N,N-diphenylpent-2-enamide. $^1$H NMR (400 MHz, CDCl$_3$) δ 7.38-7.23 (m, 10H), 6.09 (dd, 1H, J=12.0, 6.0 Hz), 5.82 (d, 1H, J=12.0 Hz), 4.88-4.85 (m, 1H), 1.35 (d, 1H, J=6.8 Hz).

Step 4: (E)-(R,Z)-5-(diphenylamino)-5-oxopent-3-en-2-yl 4-oxohex-2-enoate: NMM (91 mL, 814 mmol) was added to (E)-4-oxohex-2-enoic acid (58 g, 450 mmol) in anhydrous toluene (800 mL) at 0° C. Then, pivaloyl chloride (55 mL, 450 mmol) was added dropwise while maintaining the internal temperature between 0-5° C. After the addition, the reaction was stirred at 0° C. for 30 min. (R,Z)-4-Hydroxy-N,N-diphenylpent-2-enamide (100 g, 370 mmol) and DMAP (4.57 g, 37 mmol) in anhydrous toluene (400 mL) and anhydrous THF (200 mL) were added dropwise to the reaction mixture while maintaining the temperature between 0-5° C. under N$_2$. After 2 hours, the TLC (petroleum ether:ethyl acetate, 5:1) showed that the reaction was complete. 9 N H$_2$SO$_4$ (330 mL) was added dropwise to quench the reaction, while the temperature was kept between 0-5° C. The reactions were combined together and extracted with methyl tert-butyl ether and washed with saturated NaHCO$_3$. The crude product was purified by silica gel column chromatography (petroleum ether:ethyl acetate, 15:1) to give the title compound. $^1$H NMR (400 MHz, CDCl$_3$) δ 7.34-7.24 (m, 10H), 7.06 (dd, 1H, J=16.0, 4.0 Hz), 6.66 (dd, 1H, J=16.0, 4.0 Hz), 6.35-6.32 (m, 1H), 5.88-5.80 (m, 2H), 2.68-2.63 (m, 2H), 1.49-1.47 (m, 3H), 1.13-1.08 (m, 3H).

Step 5: (2E,4Z)-(R,Z)-5-(diphenylamino)-5-oxopent-3-en-2-yl 4-acetoxyhexa-2,4-dienoate: (E)-(R,Z)-5-(Diphenylamino)-5-oxopent-3-en-2-yl 4-oxohex-2-enoate (100 g, 265 mmol) and DMAP (9.5 g, 79 mmol) in Ac$_2$O (100 mL, 1.06 mol) were stirred at 50° C. for 19 h. TLC (petroleum ether:ethyl acetate, 5:1) showed the reaction was complete. The reaction was concentrated under reduced pressure at 45° C. The reaction was extracted with methyl tert-butyl ether and washed with 10% citric acid (5 L). The organic layer was washed with sat. NaHCO$_3$, brine, dried over Na$_2$SO$_4$ and filtered, the reaction was concentrated to give the title compound, which was used without further purification in the next step. $^1$H NMR (400 MHz, CDCl$_3$) δ 7.25-7.15 (m, 10H), 6.26-6.23 (m, 1H), 5.87-5.73 (m, 4H), 2.27 (s, 3H), 1.69 (d, 1H, J=6.8 Hz), 1.46 (d, 1H, J=6.4 Hz).

Step 6: (1R,3aS,6S,7R,7aS)-7-(diphenylcarbamoyl)-1,6-dimethyl-3-oxo-1,3,3a,6,7,7a-hexahydroisobenzofuran-5-yl acetate: (2E,4Z)-(R,Z)-5-(Diphenylamino)-5-oxopent-3-en-2-yl 4-acetoxyhexa-2,4-dienoate (100 g, 0.24 mol) in NMP (2.5 L) was stirred at 145° C. for 2 h. The TLC (petroleum ether:ethyl acetate, 3:1) showed the reaction was almost complete. The reaction was cooled to 50° C. and DBU (3.6 mL, 2.39 mmol) was added in one portion. After 1 h, the reaction was cooled to 20° C. and was poured to cold water (22 L). The reaction was extracted with ethyl acetate (22 L). The organic layer was washed with water (22 L×2). The combined aqueous layers were extracted with ethyl acetate (5 L×3). The organic layers were then combined together, washed with brine and dried with anhydrous Na$_2$SO$_4$. After concentration, a precipitate that had formed was washed with methyl tert-butyl ether to give the title compound. The filtrate was concentrated and purified by silica gel column chromatography (petroleum ether:CH$_2$Cl$_2$, 6:1) to give another batch of the title compound. $^1$H NMR (400 MHz, CDCl$_3$) δ 7.51-7.23 (m, 10H), 5.26 (s, 1H), 4.90-4.86 (m, 1H), 3.21-3.10 (m, 2H), 2.83 (dd, 1H, J=10.8, 3.6 Hz), 2.52-2.50 (m, 1H), 2.16 (s, 3H), 1.58 (d, 3H, J=6.0 Hz), 1.09 (d, 3H, J=6.4 Hz).

Step 7: (3R,3aS,4R,5S,7aR)-3,5-dimethyl-1,6-dioxo-N,N-diphenyloctahydroisobenzofuran-4-carboxamide: HCl (298 mL, 4 M in water) was added dropwise to (1R,3aS,6S,7R,7aS)-7-(diphenylcarbamoyl)-1,6-dimethyl-3-oxo-1,3,3a,6,7,7a-hexahydroisobenzofuran-5-yl acetate (100 g, 238 mmol) in CH$_3$OH (1 L) at 0° C. After the addition, the reaction was warmed to room temperature and stirred for another 36 h. The TLC (petroleum ether:ethyl acetate, 3:1) showed the reaction was almost complete. Methanol was removed under reduced pressure at 35° C. The reaction was extracted with CH$_2$Cl$_2$ and the organics was washed with sat. NaHCO$_3$, brine, dried over Na$_2$SO$_4$ and concentrated. The resultant residue was purified on multiple 15 g scale silica gel columns (petroleum ether: CH$_2$Cl$_2$, 6:1) to yield the title compound. MS ESI calcd. for C$_{23}$H$_{24}$NO$_4$ [M+H]$^+$ 378, found 378. $^1$H NMR (400 MHz, CDCl$_3$) δ 7.50-7.46 (m, 3H), 7.35-7.33 (m, 2H), 7.29-7.22 (m, 5H), 5.16-5.10 (m, 1H), 2.98-2.90 (m, 3H), 2.65-2.63 (m, 1H), 2.55-2.46 (m, 2H), 1.56 (d, 3H, J=5.6 Hz), 1.18-1.14 (m, 3H).

Step 8: (3R,3aS,4R,5S,7aR)-6,6-difluoro-3,5-dimethyl-1-oxo-N,N-diphenyloctahydroisobenzofuran-4-carboxamide: To a solution of (3R,3aS,4R,5S,7aR)-3,5-dimethyl-1,6-dioxo-N,N-diphenyloctahydroisobenzofuran-4-carboxamide (300.0 g, 0.79 mol) in CH$_2$Cl$_2$ (anhyd., 3 L) was added DAST (180 mL, 2.37 mol) dropwise slowly at 15-30° C. The resulting mixture was stirred overnight at 25° C. After LCMS showed the mixture was complete, the mixture was slowly poured to a solution of K$_3$PO$_4$.3H$_2$O (0.4 mol/L, 3 L) and was partitioned with water and CH$_2$Cl$_2$. The aqueous layer was extracted with CH$_2$Cl$_2$ (1000 mL×2). The combined organic layers were washed with NaHCO$_3$ (500 mL), brine (500 mL), dried over Na$_2$SO$_4$, filtered and concentrated under reduced pressure. The residue was oxidized by KMnO$_4$ (100 g) in DMAC for 2 hours, then filtered. The filtrate was extracted by EtOAc, washed with 10% CaCl$_2$ aqueous solution, and brine. The combined organic solution was dried by Na$_2$SO$_4$ and concentrated. The residue was further purified by recrystallization with ethanol (3 V) to give the title compound. $^1$H NMR (400 MHz, CDCl$_3$) δ 7.40 (m, 3H), 7.24 (m, 7H), 4.84 (m, 1H), 2.76 (m, 1H), 2.45 (m, 3H), 2.18 (m, 1H), 1.71 (m, 1H), 1.5 (d, 3H, J=5.6 Hz), 1.1 (d, 3H, J=6.5 Hz).

Step 9: (3R,3aR,4R,5S,7aR)-6,6-difluoro-3,5-dimethyl-1-oxooctahydroisobenzofuran-4-carboxylic acid: To a solution of the (3R,3aS,4R,5S,7aR)-6,6-difluoro-3,5-dimethyl-1-oxo-N,N-diphenyloctahydroisobenzofuran-4-carboxamide (260 g, 0.653 mol) in THF (1300 mL) was added a solution of LiOH.H$_2$O (55 g, 1.31 mol) in H$_2$O (650 mL) at room temperature. The mixture was heated to 60° C. and stirred for 2 h. Upon completion of reaction, the mixture was diluted with LiOH.H$_2$O solution (1.3 L, 10% in water). The THF layer was removed in vacuo. The aqueous phase was extracted with MTBE (800 mL×3). The aqueous layer was acidified to pH 1-2 with 1N HCl and extracted with EtOAc (800 mL mL×3). The combined organic layers were washed with water (500 mL), brine (500 mL), dried over Na$_2$SO$_4$, filtered and concentrated to give the title compound. $^1$H NMR (400 MHz, CDCl$_3$) δ 4.73 (m, 1H), 2.99 (m, 1H), 2.89 (m, 1H), 2.64 (m, 1H), 2.53 (m, 1H), 2.33 (m, 1H), 1.86 (m, 1H), 1.39 (d, 3H), 1.15 (d, 3H).

Step 10: (3R,3aS,4R,5S,7aR)-6,6-difluoro-4-(hydroxymethyl)-3,5-dimethylhexahydroisobenzofuran-1(3H)-one:
To a solution of (3R,3aR,4R,5S,7aR)-6,6-difluoro-3,5-dimethyl-1-oxooctahydroisobenzofuran-4-carboxylic acid (81.0 g, 0.326 mol) in CH$_2$Cl$_2$ (800 mL) was added (COCl)$_2$ (58.8 mL, 0.66 mol) and DMF (1 mL) at 20-25° C. under nitrogen. The mixture was stirred for 4 hours. Upon reaction completion, the mixture was concentrated under reduced pressure. The residue was dissolved with THF (400 mL×2) and then concentrated twice. The residue was dissolved in THF (500 mL), and a solution of LiAlH(t-BuO)$_3$ (653 mL, 0.653 mol, 1 M in THF) was added dropwise slowly below −55° C. under nitrogen. The mixture was slowly warmed to room temperature and stirred overnight. Upon reaction completion, the mixture was quenched with 1N HCl (1 L) and extracted with EtOAc (500 mL×3). The combined organic layers were washed with water (500 mL), brine (500 mL), dried over Na$_2$SO$_4$, filtered and concentrated to give the title compound. $^1$H NMR (400 MHz, CDCl$_3$) δ 4.77 (m, 1H), 3.83 (m, 2H), 2.85 (m, 1H), 2.45 (m, 2H), 2.07 (m, 2H), 1.83 (m, 1H), 1.59 (d, 3H), 1.13 (d, 3H).

SCHEME B

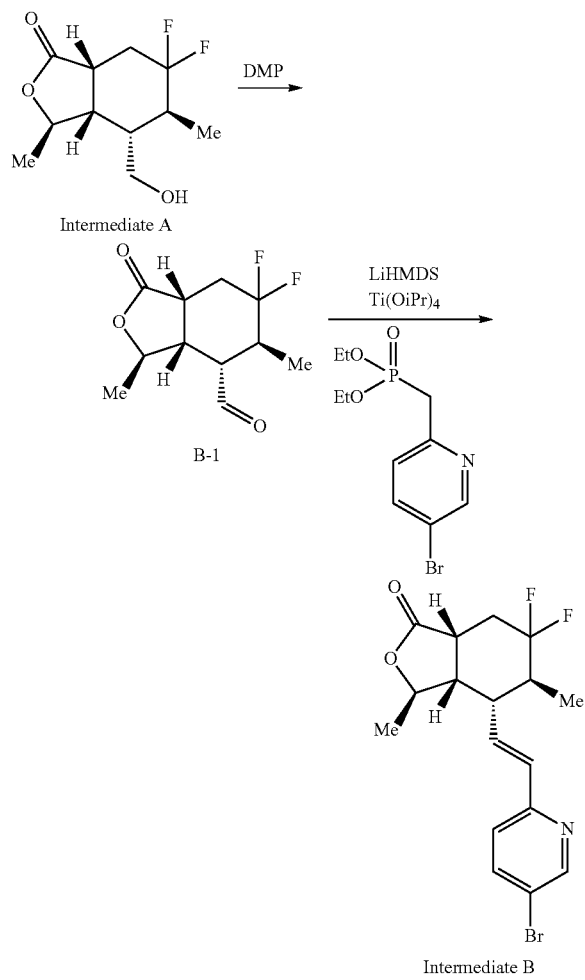

Intermediate B can be prepared according to Scheme B through a two-step process. Oxidation of intermediate A to aldehyde (B-1) and Horner-Wadsworth-Emmons olefination reaction with known or synthesized phosphonate esters provided Intermediate B.

Intermediate B

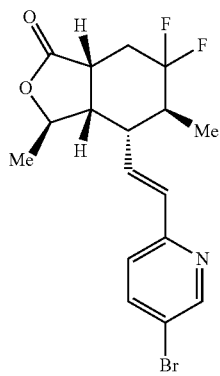 [SMILES: C[C@H]1OC(=O)[C@@H]2CC(F)(F)[C@@H](C)[C@H](/C=C/c3ccc(Br)cn3)[C@H]12]

Step 1: (3R,3aS,4R,5S,7aR)-6,6-difluoro-3,5-dimethyl-1-oxooctahydroisobenzofuran-4-carbaldehyde: To a stirred solution of (3R,3aS,4R,5S,7aR)-6,6-difluoro-4-(hydroxymethyl)-3,5-dimethylhexahydroisobenzofuran-1(3H)-one (56 g, 0.24 mol) in MeCN (600 mL) was added Dess-Martin reagent (122 g, 0.287 mol) and NaHCO$_3$ (60.3 g, 227 mol) under nitrogen at 0° C. The mixture was stirred for 4 h at 25° C. Upon reaction completion, the mixture was transferred to into L-ascorbic acid (5% aq., 1500 mL) under nitrogen, and then was filtered. The filtrate was quenched with Na$_2$SO$_3$ (5% aq., 750 mL). The solvent was removed and the product was extracted with EtOAc (750 mL×3). The combined organic layers were washed with brine (900 mL), dried over Na$_2$SO$_4$, filtered and concentrated to give the title compound, which was directly used in the next step without further purification.

Step 2: (3R,3aS,4R,5S,7aR)-4-((E)-2-(5-bromopyridin-2-yl)vinyl)-6,6-difluoro-3,5-dimethylhexahydroisobenzofuran-1(3H)-one: To a solution of diethyl ((5-bromopyridin-2-yl)methyl)phosphonate (95.6 g, 0.310 mol) in THF (400 mL) was added LiHMDS (310 mL, 0.310 mol, 1 M in THF) dropwise at 0° C. under nitrogen. The mixture was stirred for 30 min at 0° C., and then warmed up to about 25° C. Ti(OiPr)$_4$ (110 g, 0.3103 mmol) was added and the reaction was stirred for 30 min at 25° C. A solution of (3R,3aS,4R,5S,7aR)-6,6-difluoro-3,5-dimethyl-1-oxooctahydroisobenzofuran-4-carbaldehyde (36 g, 0.1552 mmol) in THF (400 mL) was added into the mixture, and stirred overnight at room temperature. Upon reaction completion, the mixture was quenched with saturated solution of potassium sodium tartrate (1 L), and then filtered. The filtrate was extracted with EtOAc (500 mL×3). The combined organic layers were washed with brine (500 mL), dried over Na$_2$SO$_4$, filtered and concentrated. The residue was purified by column chromatography with PE/EtOAc (20:1) to give the title compound. MS ESI calcd. for C$_{17}$H$_{19}$BrF$_2$NO$_2$ [M+H]$^+$ 386/388, found 386/388. $^1$H NMR (500 MHz, CDCl$_3$) δ 8.61 (d, 1H, J=2 Hz), 7.78 (dd, 1H, J=2.4, 8.4 Hz), 7.09 (d, 1H, J=8.4 Hz), 6.55 (m, 2H), 4.74 (m, 1H), 2.95 (m, 1H), 2.73 (m, 1H), 2.38-2.53 (m, 2H), 1.83-2.04 (m, 2H), 1.45 (d, 3H, J=6 Hz), 1.07 (d, 3H, J=6.8 Hz).

SCHEME C

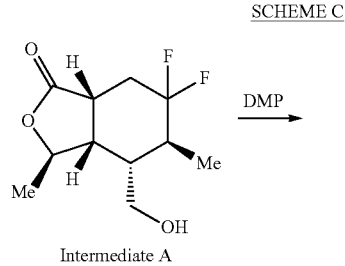

Intermediate A

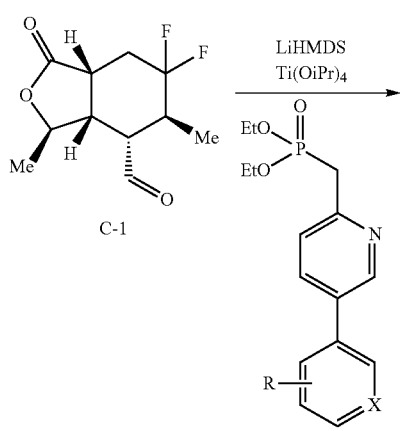

C-1

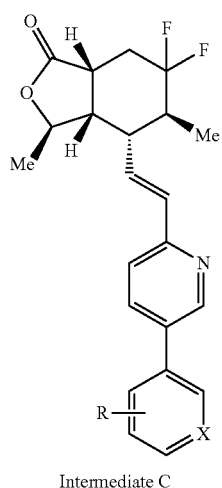

Intermediate C where X is C or N; and R is $R^2$ or $R^5$

Intermediate C can be prepared according to scheme C through an oxidation to aldehyde C-1 and a Horner-Wadsworth-Emmons olefination reaction using known or synthesized phosphonate esters from Intermediate A.

Intermediate C1

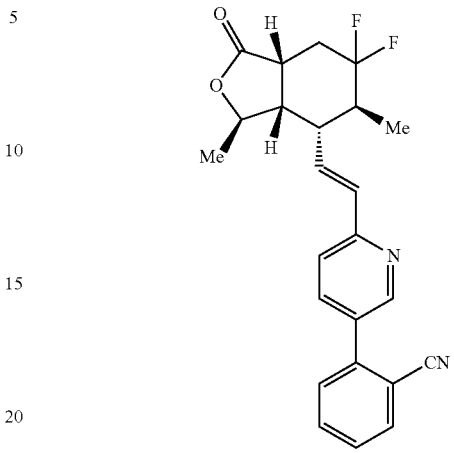

Step 1: (3R,3aS,4R,5S,7aR)-6,6-difluoro-3,5-dimethyl-1-oxooctahydroisobenzofuran-4-carbaldehyde: To a solution of (3R,3aS,4R,5S,7aR)-6,6-difluoro-4-(hydroxymethyl)-3,5-dimethylhexahydroisobenzofuran-1(3H)-one (3.21 g, 13.70 mmol) in $CH_2Cl_2$ (100 mL) stirred at 0° C. under nitrogen was added DMP (8.72 g, 20.56 mmol). The reaction mixture was stirred for 2 h. Upon reaction completion, the mixture was quenched with $NaHCO_3$ (5% aq., 200 mL) and $Na_2SO_3$ (5% aq., 200 mL) and extracted with $CH_2Cl_2$ (3×150 mL). The combined organic layers were washed with brine (80 mL), dried over anhyd. $Na_2SO_4$ and concentrated under reduced pressure to afford the title compound. MS ESI calcd. for $C_{11}H_{15}F_2O_3$ $[M+H]^+$ 233, found 233.

Step 2: 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile: To a solution of diethyl ((5-(2-cyanophenyl)pyridin-2-yl)methyl)phosphonate (1.98 g, 6.0 mmol) in THF (10 mL) at 0° C. was added lithium bis(trimethylsilyl)amide (6.0 mL, 6.0 mmol, 1 M in THF). The reaction was stirred for 30 minutes at 0° C. before allowing it to warm to RT. Titanium(IV) isopropoxide (1.76 mL, 6.0 mmol) was added to the reaction mixture. The reaction mixture was stirred for 5 min., then a solution of (3R,3aS,4R,5S,7aR)-6,6-difluoro-3,5-dimethyl-1-oxooctahydroisobenzofuran-4-carbaldehyde (0.697 g, 3.0 mmol) in THF (10 mL) was added and stirred at RT for 1 hour. The reaction was quenched with aqueous sat. potassium sodium tartrate and the product was extracted with EtOAc. The organic phase was dried with $Na_2SO_4$, concentrated and purified by silica gel chromatography (0-40% EtOAc in hexanes) to provide 2-(6-((E)-2-((3R,3aS,4R,5S,7aR)-6,6-difluoro-3,5-dimethyl-1-oxooctahydro isobenzofuran-4-yl)vinyl)pyridin-3-yl)benzonitrile. MS ESI calcd. for $C_{24}H_{23}F_2N_2O_2$ $[M+H]^+$ 409, found 409. $^1$H NMR (500 MHz, $CDCl_3$) δ 8.75 (d, J=2.3 Hz, 1 H); 7.97 (d, J=8.0 Hz, 1 H); 7.86 (d, J=7.8 Hz, 1 H); 7.75 (t, J=7.7 Hz, 1 H); 7.56 (t, J=7.7 Hz, 2 H); 7.37 (d, J=8.1 Hz, 1H); 6.69-6.71 (m, 2 H); 4.80 (m, 1 H); 2.97-3.02 (m, 1 H); 2.79-2.84 (m, 1 H); 2.53-2.60 (m, 1 H); 2.41-2.49 (m, 1 H); 2.02-2.16 (m, 1 H); 1.85-1.99 (m, 1 H); 1.53 (d, J=6.0 Hz, 3 H), 1.13 (d, J=6.6 Hz, 3 H).

The following compound in Table 1 was prepared according to Scheme C using the procedure outlined in the synthesis intermediate C1 using known or synthesized phosphonate esters.

TABLE 1

| Intermediate | Structure | IUPAC Name | Exact Mass [M + H]+ |
|---|---|---|---|
| C2 | 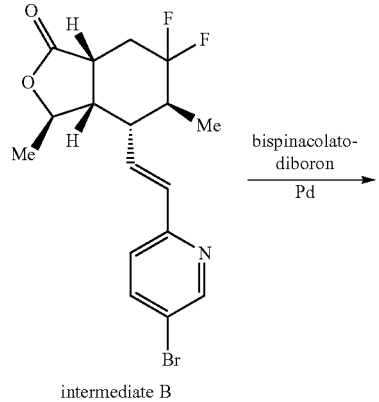 | (3R,3aS,4R,5S,7aR)-6,6-difluoro-4-((E)-2-(5-(3-fluorophenyl)pyridin-2-yl)vinyl)-3,5-dimethylhexahydroisobenzofuran-1(3H)-one | 402 |

SCHEME D

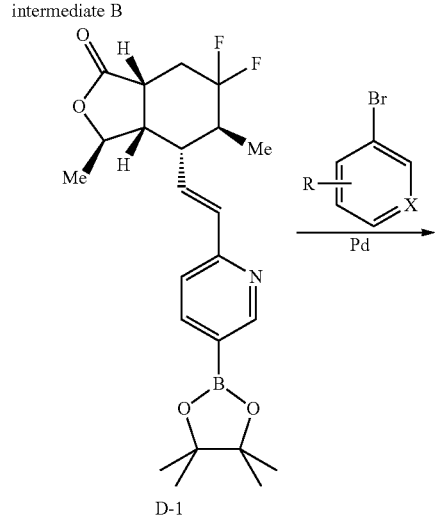

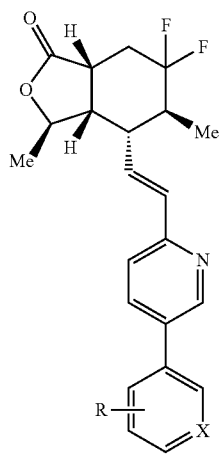

intermediate D where X is C or N; and R is $R^2$ or $R^5$

Intermediate D can be prepared via a Miyaura reaction with Intermediate B to yield boronic ester (D-1) according to scheme D. Subsequent palladium-mediated coupling provides intermediate D.

Intermediate D1

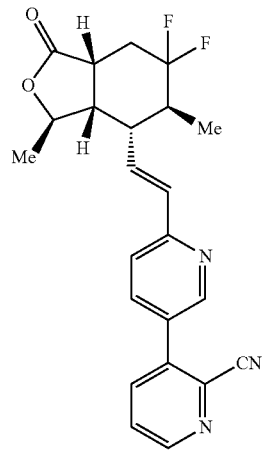 [SMILES: C[C@H]1OC(=O)[C@@H]2CC(F)(F)[C@@H](C)[C@H](/C=C/c3ccc(-c4cccnc4C#N)cn3)[C@H]12]

Step 1: (3R,3aS,4R,5S,7aR)-6,6-difluoro-3,5-dimethyl-4-((E)-2-(5-(4,4,5,5-tetramethyl-1,3,2-dioxaborolan-2-yl)pyridin-2-yl)vinyl)hexahydroisobenzofuran-1(3H)-one:

In a reaction vessel (3R,3aS,4R,5S,7aR)-4-((E)-2-(5-bromopyridin-2-yl)vinyl)-6,6-difluoro-3,5-dimethylhexahydroisobenzofuran-1(3H)-one (2.0 g, 5.18 mmol), bispinacolatodiboron (1.64 g, 6.47 mmol), and potassium acetate (1.01 g, 10.4 mmol) were combined. This mixture was then evacuated and backfilled with $N_2$ (3 times). Then dry, degassed dioxane (25.9 mL) was added to this flask. This mixture was then heated at 90° C. for 12 h. The mixture was cooled, diluted with acetonitrile (40 mL) and filtered through a 10 g plug of C18 silica gel pad. The solvent was evaporated under reduced pressure to provide the title compound, which was used without further purification. MS ESI calcd. for $C_{17}H_{21}BF_2NO_4$ [M+H]$^+$ (ionizes for boronic acid) 352, found 352.

Step 2: 6'-((E)-2-((3R,3aS,4R,5S,7aR)-6,6-difluoro-3,5-dimethyl-1-oxooctahydroiso benzofuran-4-yl)vinyl)-[3,3'-bipyridine]-2-carbonitrile: To a mixture of (3R,3aS,4R,5S,7aR)-6,6-difluoro-3,5-dimethyl-4-((E)-2-(5-(4,4,5,5-tetramethyl-1,3,2-dioxaborolan-2-yl)pyridin-2-yl)vinyl) hexahydroisobenzofuran-1(3H)-one (1.0 g, 2.31 mmol), 3-bromopicolinonitrile (0.549 g, 3.00 mmol) and potassium carbonate (0.96 g, 6.92 mmol) in dioxane (12 mL) was added 1,1'-bis(di-tert-butylphosphino)ferrocene palladium dichloride (0.150 g, 0.231 mmol) at rt. The reaction mixture was stirred at 60° C. for 1 hour. After cooling to 25° C., the reaction was diluted with EtOAc (200 mL) and partitioned with brine (200 mL). The organics were washed again with brine, dried over anhydrous sodium sulfate, filtered and evaporated. Purification by silica gel chromatography (25-75% EtOAc/hexanes) provided the title compound. MS ESI calcd. for $C_{23}H_{22}F_2N_3O_2$ [M+H]$^+$ 410, found 410.

The following intermediate in Table 2 was prepared according to scheme D using the procedure outlined in the synthesis intermediate D1 using known or commerically available aryl bromides.

TABLE 2

| Intermediate | Structure | IUPAC Name | Exact Mass [M + H]+ |
|---|---|---|---|
| D2 | 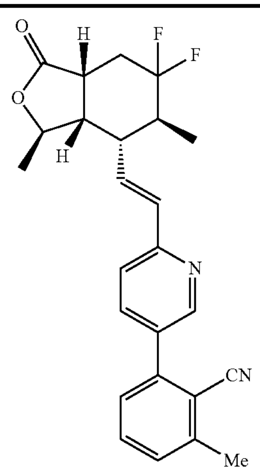 | 2-(6-((E)-2-((3R,3aS,4R,5S,7aR)-6,6-difluoro-3,5-dimethyl-1-oxooctahydro isobenzo furan-4-yl)vinyl)pyridin-3-yl)-6-methylbenzonitrile | 423 |

General Synthetic Schemes

Representative compounds of the present invention can be synthesized according to the general schemes outlined below as well as the representative examples that follow. Since the schemes are an illustration, the invention should not be construed as being limited by the chemical reactions and conditions expressed. The preparation of the various starting materials used in the schemes is well within the ordinary skill level of a practitioner of this art.

SCHEME 1

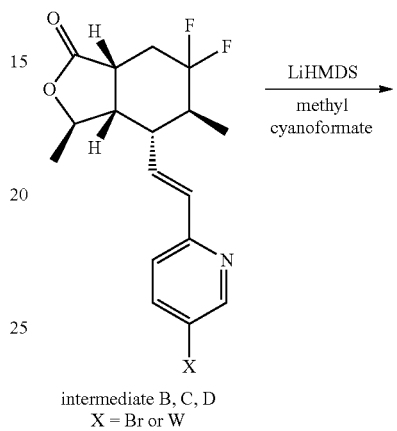

intermediate B, C, D
X = Br or W

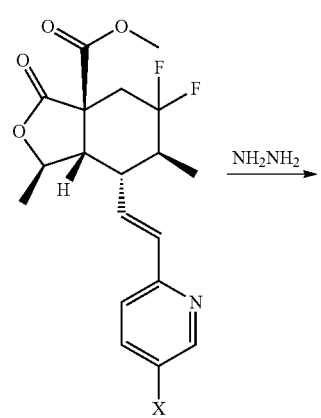

1-1

1-2

1

A = O or NH₂

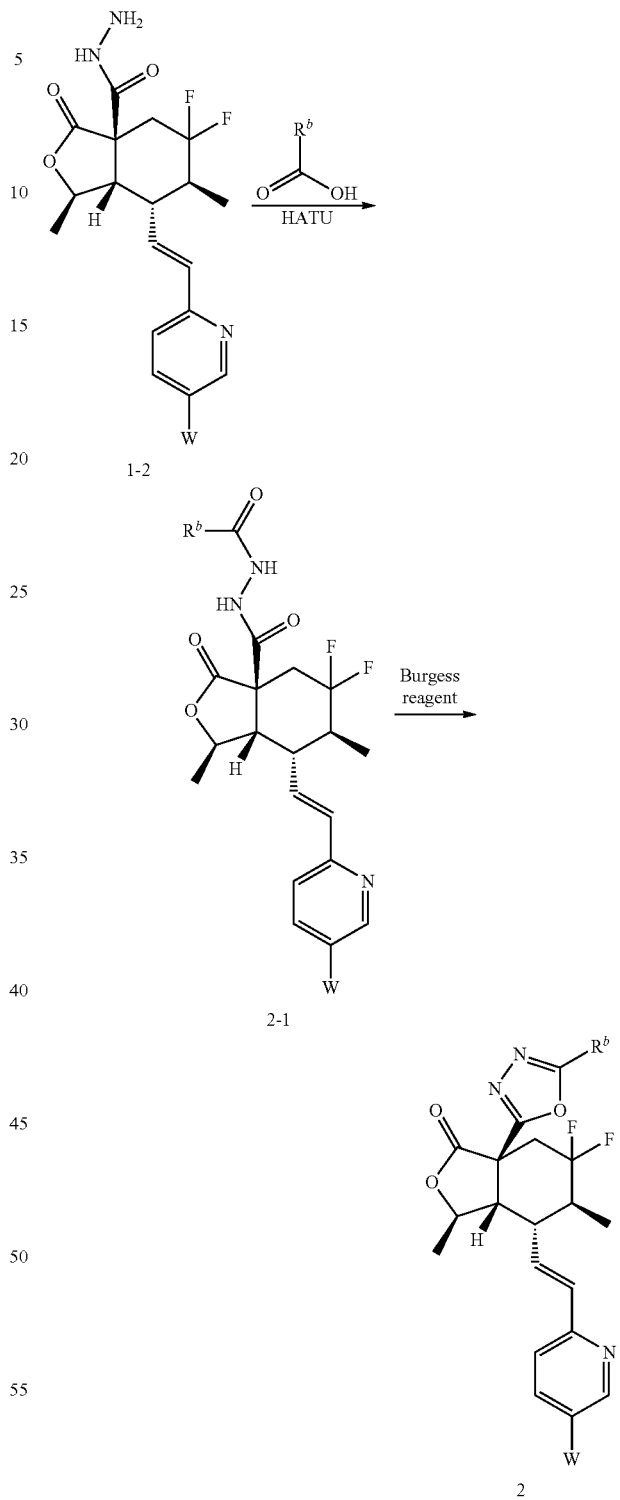

SCHEME 2

1-2

2-1

2

Compounds of Formula (1) can be prepared via modification of intermediate B, C or D by generating the corresponding anion of using bases such as LiHMDS and reaction with an appropriate electrophile to yield (1-1). Subsequent exposure to hydrazine yielded the corresponding hydrazide (1-2) and reaction with CDI or cyanogen bromide provided compounds of Formula 1.

Compounds of Formula (2) can be prepared from hydrazide (1-2), which was a synthetic intermediate formed in Scheme 1. Amide coupling conditions using HATU and various carboxylic acids provides oxazole precursor (2-1). Condensation under the action of Burgess reagent, furnished compound of Formula (2).

SCHEME 3

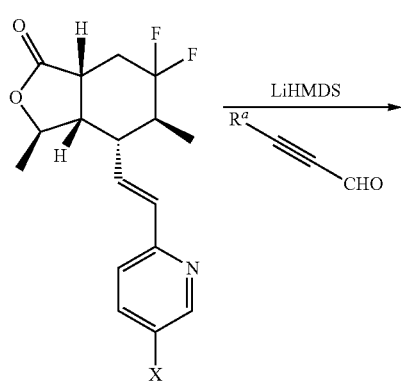

intermediate B, C, D
X = Br or W

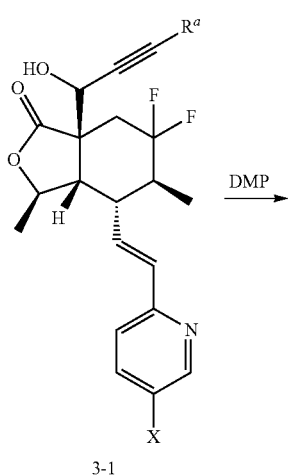

3-1

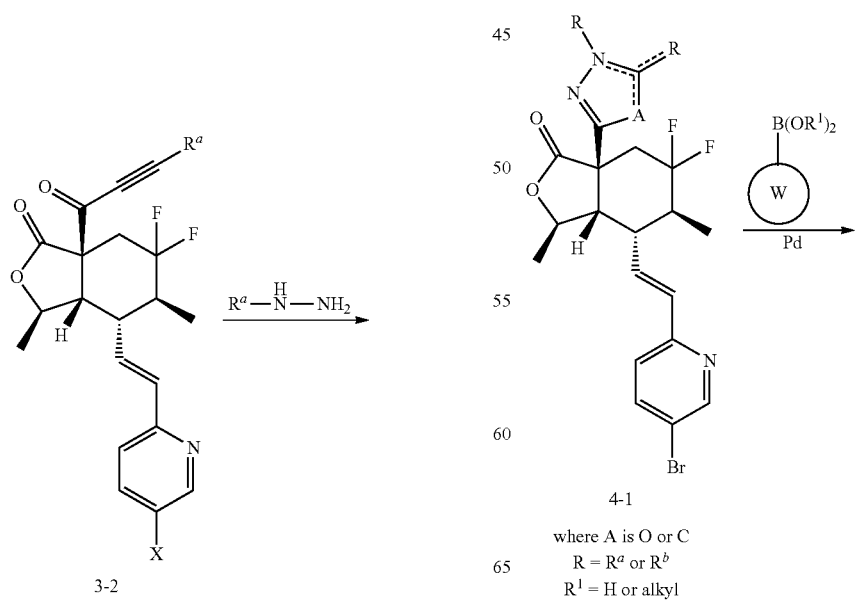

3-2

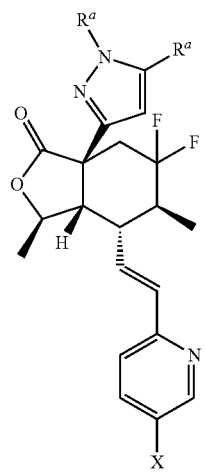

3

Compounds of Formula (3) can be prepared via modification of intermediate B, C or D by generating the corresponding anion using bases, such as LiHMDS and reaction with an appropriate electrophile to yield (3-1). Subsequent oxidation to ynone (3-2) and exposure to a hydrazine yielded compounds of Formula (3).

SCHEME 4

4-1 where A is O or C
R = $R^a$ or $R^b$
$R^1$ = H or alkyl

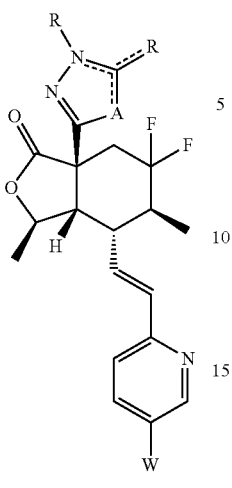

4

Compounds of Formula 4 can be prepared from intermediates generated using in Schemes 1 or 3 from intermediate B. A palladium-mediated Suzuki coupling reaction of bromide (4-1) with known or commerically available boronic acids or esters furnished compounds of the Formula 4.

EXAMPLES

The following schemes and examples are provided so that the invention will be more fully appreciated and understood. Starting materials are made using known procedures or as illustrated below.

Example 1

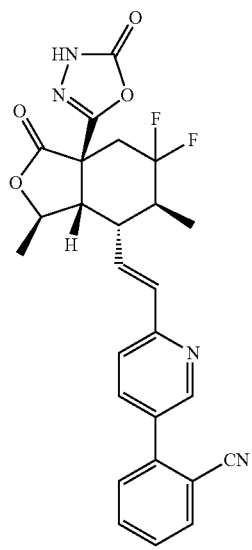 [SMILES: C[C@H]1OC(=O)[C@]2(c3n[nH]c(=O)o3)CC(F)(F)[C@@H](C)[C@H](/C=C/c3ccc(-c4ccccc4C#N)cn3)[C@H]12]

Step 1: (1R,3aR,6S,7R,7aS)-7-((E)-2-(5-(2-cyanophenyl) pyridin-2-yl)vinyl)-5,5-difluoro-1,6-dimethyl-3-oxoocta-hydroisobenzofuran-3a-carboxamide: To 2-(6-((E)-2-((3R,3aS,4R,5S,7aR)-6,6-difluoro-3,5-dimethyl-1-oxooctahydroiso benzofuran-4-yl)vinyl)pyridin-3-yl) benzonitrile (0.90 g, 2.20 mmol) in 2-Me-THF (7 mL) at 0° C. under $N_2(g)$ was added lithium bis(trimethylsilyl) amide (461 mg, 2.75 mmol). The reaction mixture was stirred at 0° C. for 30 min before cooling the system to −78° C., and adding methyl cyanoformate (0.244 g, 2.86 mmol). After stirring for 40 min at −78° C., the reaction mixture was allowed to warmed to RT and was stirred for 20 min. The reaction mixture was cooled to 0° C., quenched with saturated $NH_4Cl_{(aq)}$, and the product was extracted with EtOAc. The organic phase was washed with brine, dried with $Na_2SO_4$, and was concentrated. The residue was purified by column chromatography on silica (0-40% EtOAc in hexanes) to afford the title compound. MS ESI calcd. for $C_{26}H_{25}F_2N_2O_4$ [M+H]$^+$ 467, found 467.

Step 2: (1R,3aR,6S,7R,7aS)-7-((E)-2-(5-(2-cyanophenyl) pyridin-2-yl)vinyl)-5,5-difluoro-1,6-dimethyl-3-oxoocta-hydroisobenzofuran-3a-carbohydrazide: To a solution of (1R,3aR,6S,7R,7aS)-7-((E)-2-(5-(2-cyanophenyl)pyridin-2-yl)vinyl)-5,5-difluoro-1,6-dimethyl-3-oxooctahy-droisobenzofuran-3a-carboxamide (161 mg, 0.345 mmol) in ethanol (2.5 mL) was added hydrazine (0.108 mL, 3.45 mmol). The reaction was heated and stirred at 60° C. for 30 min. Upon completion of the reaction, the system was cooled to RT and was diluted with EtOAc, was washed with water, and brine. The organic phase was dried with $Na_2SO_4$ before concentrating and the residue was purified by column chromatography on silica (0-65% EtOAc in hexanes) to provide the title compound. MS ESI calcd. for $C_{25}H_{25}F_2N_4O_4$ [M+H]$^+$ 467, found 467.

Step 3: 2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl) benzonitrile: A solution of (1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carbohydrazide (35 mg, 0.075 mmol) and 1,1'-carbonyldiimidazole (48.7 mg, 0.300 mmol) in THF (0.75 mL) was stirred at 25° C. for 1 hour. Upon reaction completion, the solvent was removed under reduced pressure and the residue was purified by reverse phase HPLC (acetonitrile/water with 0.1% TFA modifier) to yield the title compound as a TFA salt. MS ESI calcd. for $C_{26}H_{23}F_2N_4O_4$ [M+H]$^+$ 493, found 493. $^1$H NMR (500 MHz, CDCl$_3$) δ 9.12 (br s, 1 H); 8.98 (d, J=8.35, 1 H); 8.30 (d, J=8.3 Hz, 1 H); 7.90 (d, J=7.8 Hz, 1 H); 7.80 (d, J=7.7 Hz, 1 H); 7.64 (t, J=7.6 Hz, 3 H); 6.90 (d, J=9.7 Hz, 1 H); 6.81-6.95 (m, 1 H); 4.84-4.96 (m, 1 H); 3.06-3.18 (m, 2 H); 2.84-2.96 (m, 1 H); 2.12-2.33 (m, 2 H); 1.60 (d, J=9.0, 3 H); 1.12 (d, J=6.6 Hz, 3 H). PAR-1 FLIPR IC$_{50}$=4.22 nM.

The following examples in Table 3 were prepared according to Scheme 1 using the procedure outlined in the synthesis of Example 1. Intermediate C or D may be used in step 1. In step 3, cyanogen bromide (1 equivalent) with aqueous sodium bicarbonate (1 equivalent, 2 M) can be utilized to provide the corresponding 1,3,4-oxadiazol-2-amine.

TABLE 3
| Ex | Structure | IUPAC Name | Exact Mass [M + H]+ | PAR-1 FLIPR IC$_{50}$ (nM) |
|---|---|---|---|---|
| 2 | 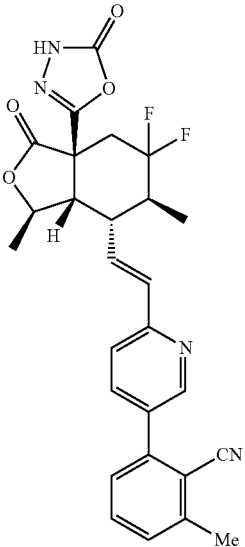 [SMILES: Cc1cccc(-c2ccc(/C=C/[C@@H]3[C@@H]4[C@@H](C)OC(=O)[C@]4(c4n[nH]c(=O)o4)CC(F)(F)[C@H]3C)nc2)c1C#N] | 2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl)-6-methylbenzonitrile | 507 | 1.34 |
| 3 | 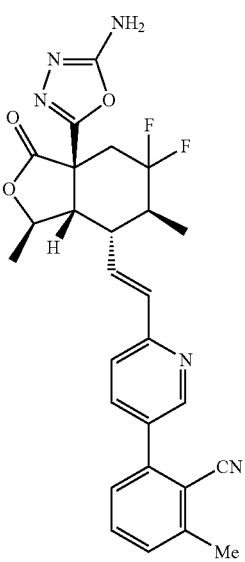 [SMILES: Cc1cccc(-c2ccc(/C=C/[C@@H]3[C@@H]4[C@@H](C)OC(=O)[C@]4(c4nnc(N)o4)CC(F)(F)[C@H]3C)nc2)c1C#N] | 2-(6-((E)-2-((3R,3aS,4R,5S,7aR)-7a-(5-amino-1,3,4-oxadiazol-2-yl)-6,6-difluoro-3,5-dimethyl-1-oxooctahydroisobenzofuran-4-yl)vinyl)pyridin-3-yl)-6-methylbenzonitrile | 506 | 1.22 |

TABLE 3-continued

| Ex | Structure | IUPAC Name | Exact Mass [M + H]+ | PAR-1 FLIPR IC$_{50}$ (nM) |
|---|---|---|---|---|
| 4 | 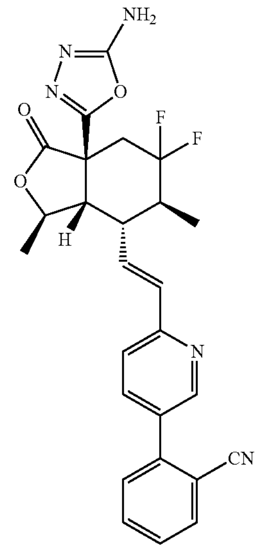 [SMILES: C[C@H]1OC(=O)[C@]2(c3nnc(N)o3)CC(F)(F)[C@@H](C)[C@H](/C=C/c3ccc(-c4ccccc4C#N)cn3)[C@H]12] | 2-(6-((E)-2-((3R,3aS,4R,5S,7aR)-7a-(5-amino-1,3,4-oxadiazol-2-yl)-6,6-difluoro-3,5-dimethyl-1-oxooctahydroisobenzofuran-4-yl)vinyl)pyridin-3-yl)benzonitrile | 492 | 3.08 |

Example 5

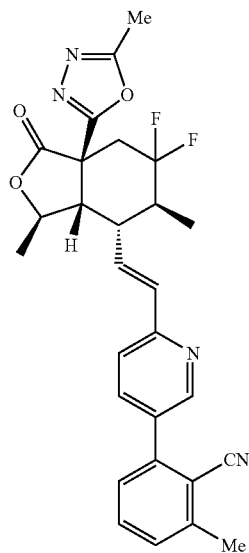 [SMILES: Cc1nnc([C@@]23CC(F)(F)[C@@H](C)[C@H](/C=C/c4ccc(-c5cccc(C)c5C#N)cn4)[C@@H]2[C@@H](C)OC3=O)o1]

Step 1: (1R,3aR,6S,7R,7aS)-N'-acetyl-7-((E)-2-(5-(2-cyano-3-methylphenyl)pyridin-2-yl)vinyl)-5,5-difluoro-1,6-dimethyl-3-oxooctahydroisobenzofuran-3a-carbohydrazide: A solution of HATU (32.9 mg, 0.087 mmol), DIEA (0.023 mL, 0.133 mmol), acetic acid (4.77 µL, 0.083 mmol) in DMF (0.5 mL) was stirred at 25° C. for 10 min. (1R,3aR,6S,7R,7aS)-7-((E)-2-(5-(2-Cyano-3-methylphenyl)pyridin-2-yl)vinyl)-5,5-difluoro-1,6-dimethyl-3-oxooctahydroisobenzofuran-3a-carbohydrazide (32 mg, 0.067 mmol) was added to the reaction mixture and was stirred for 1 hour at 25° C. The reaction was then diluted with EtOAc, washed with water and brine. The organic phase was dried with Na$_2$SO$_4$ and was concentrated. The crude residue was purified by column chromatography (0 to 5% MeOH in DCM) to provide the title compound. MS ESI calcd. for C$_{30}$H$_{33}$F$_2$N$_2$O$_4$ [M+H]$^+$ 523, found 523.

Step 2: 2-(6-((E)-2-((3R,3aS,4R,5S,7aR)-6,6-difluoro-3,5-dimethyl-7a-(5-methyl-1,3,4-oxadiazol-2-yl)-1-oxooctahydroisobenzofuran-4-yl)vinyl)pyridin-3-yl)-6-methylbenzonitrile: In a microwave vial, was added Burgess reagent (21.89 mg, 0.092 mmol), (1R,3aR,6S,7R,7aS)-N'-acetyl-7-((E)-2-(5-(2-cyano-3-methylphenyl)pyridin-2-yl)vinyl)-5,5-difluoro-1,6-dimethyl-3-oxooctahydroisobenzofuran-3a-carbohydrazide (16 mg, 0.031 mmol) and THF (0.75 mL). The microwave tube was capped and heated at 150° C. for 30 min. in a microwave. The reaction mixture was diluted with EtOAc, washed with water and brine. The organic phase was dried with Na$_2$SO$_4$, concentrated and the crude was purified by reverse phase HPLC (acetonitrile/water with 0.1% TFA modifier) to provide the title compound as a TFA salt. MS ESI calcd. for C$_{28}$H$_{27}$F$_2$N$_4$O$_3$ [M+H]$^+$ 505, found 505. $^1$H NMR (500 MHz, CD$_3$OD) δ 8.88 (d, J=6.1 Hz, 1H); 8.39 (t, J=8.9 Hz, 1 H); 8.01 (t, J=9.2 Hz, 1 H); 7.72 (td, J=7.8, 3.7 Hz, 1 H); 7.50-7.57 (m, 2 H); 6.90-6.99 (m, 2 H); 5.19 (m, 1 H); 3.33 (br m, 2H); 3.00 (d, J=10.6 Hz, 2 H); 2.63-2.65 (m, 6H); 2.49 (br m, 1 H); 1.56 (dd, J=5.6, 2.5 Hz, 3 H); 1.04 (dd, J=5.01, 2.98 Hz, 3 H). PAR-1 FLIPR IC$_{50}$=2.45 nM.

The following examples in Table 4 were prepared according to Scheme 2 using the procedure outlined in the synthesis of Example 5. Intermediate C or D may be used in step 1.

TABLE 4

| Ex | Structure | IUPAC Name | Exact Mass [M + H]+ | PAR-1 FLIPR IC$_{50}$ (nM) |
|---|---|---|---|---|
| 6 | 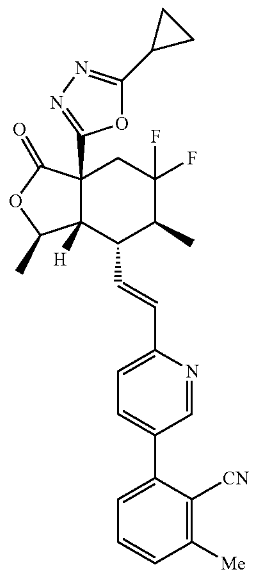 [SMILES: Cc1cccc(-c2ccc(/C=C/[C@@H]3[C@@H]4[C@@H](C)OC(=O)[C@]4(c4nnc(C5CC5)o4)CC(F)(F)[C@H]3C)nc2)c1C#N] | 2-(6-((E)-2-((3R,3aS,4R,5S,7aR)-7a-(5-cyclopropyl-1,3,4-oxadiazol-2-yl)-6,6-difluoro-3,5-dimethyl-1-oxooctahydroisobenzofuran-4-yl)vinyl)pyridin-3-yl)-6-methylbenzonitrile | 531 | 2.07 |
| 7 | 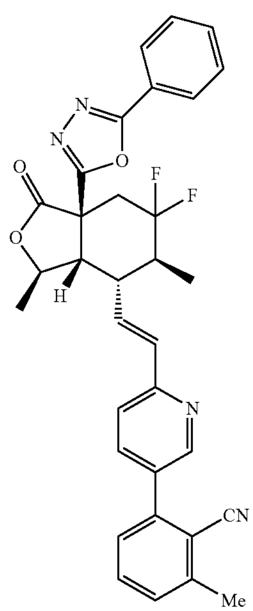 [SMILES: Cc1cccc(-c2ccc(/C=C/[C@@H]3[C@@H]4[C@@H](C)OC(=O)[C@]4(c4nnc(-c5ccccc5)o4)CC(F)(F)[C@H]3C)nc2)c1C#N] | 2-(6-((E)-2-((3R,3aS,4R,5S,7aR)-6,6-difluoro-3,5-dimethyl-1-oxo-7a-(5-phenyl-1,3,4-oxadiazol-2-yl)octahydroisobenzofuran-4-yl)vinyl)pyridin-3-yl)-6-ethylbenzonitrile | 567 | 5.01 |

Example 8

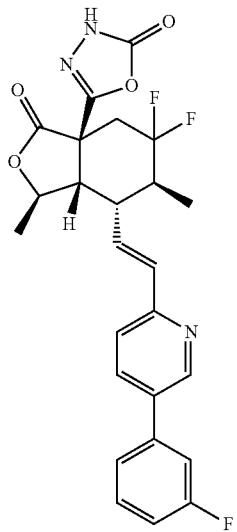 [SMILES: C[C@H]1OC(=O)[C@]2(c3n[nH]c(=O)o3)CC(F)(F)[C@@H](C)[C@H](/C=C/c3ccc(-c4cccc(F)c4)cn3)[C@H]12]

Step 1: (1R,3aR,6S,7R,7aS)-methyl-7-((E)-2-(5-bromopyridin-2-yl)vinyl)-5,5-difluoro-1,6-dimethyl-3-oxooctahydroisobenzofuran-3a-carboxylate: To (3R,3aS,4R,5S,7aR)-4-((E)-2-(5-bromopyridin-2-yl)vinyl)-6,6-difluoro-3,5-dimethylhexahydroisobenzofuran-1(3H)-one (3.86 g, 10.0 mmol) in THF (30 mL) at 0° C. under $N_2(g)$ was added lithium bis(trimethylsilyl)amide (12.5 mL, 12.5 mmol, 1 M in THF). The reaction mixture was stirred at 0° C. for 30 min before cooling the system to −78° C., and adding methyl cyanoformate (1.11 g, 13.0 mmol). After stirring for 40 min at −78° C., the reaction mixture was allowed to warmed to RT and was stirred for 20 min. The reaction mixture was cooled to 0° C., quenched with saturated $NH_4Cl_{(aq)}$, and the product was extracted with EtOAc. The organic phase was washed with brine, dried with $Na_2SO_4$, and was concentrated. The residue was purified by column chromatography on silica (0-40% EtOAc in hexanes) to afford the title compound. MS ESI calcd. for $C_{19}H_{21}BrF_2NO_4$ [M+H]$^+$ 444/446, found 444/446.

Step 2: (1R,3aR,6S,7R,7aS)-7-((E)-2-(5-bromopyridin-2-yl)vinyl)-5,5-difluoro-1,6-dimethyl-3-oxooctahydroisobenzofuran-3a-carbohydrazide: To a solution of (1R,3aR,6S,7R,7aS)-methyl-7-((E)-2-(5-bromopyridin-2-yl)vinyl)-5,5-difluoro-1,6-dimethyl-3-oxooctahydroisobenzofuran-3a-carboxylate (311 mg, 0.7 mmol) in ethanol (3.0 mL) was added hydrazine (0.264 mL, 8.40 mmol). The reaction was heated and stirred at 50° C. for 30 min. Upon completion of the reaction, the system was cooled to RT and was diluted with EtOAc, was washed with water, and brine. The organic phase was dried with $Na_2SO_4$ before concentrating and the residue was purified by column chromatography on silica (0-40% EtOAc in hexanes) to provide the title compound. MS ESI calcd. for $C_{18}H_{21}BrF_2N_3O_3$ [M+H]$^+$ 444/446, found 444/446.

Step 3: 5-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)-1,3,4-oxadiazol-2(3H)-one: A solution of ((1R,3aR,6S,7R,7aS)-7-((E)-2-(5-bromopyridin-2-yl)vinyl)-5,5-difluoro-1,6-dimethyl-3-oxooctahydroisobenzofuran-3a-carbohydrazide (133 mg, 0.3 mmol) and 1,1'-carbonyldiimidazole (195 mg, 1.200 mmol) in THF (1.5 mL) was stirred at 25° C. for 1 hour. Upon reaction completion, the solvent was removed under reduced pressure and the residue was purified by silica gel chromatography (0-30% EtOAc in hexanes) to yield the title compound. MS ESI calcd. for $C_{19}H_{19}BrF_2N_3O_4$ [M+H]$^+$ 470/472, found 470/472.

Step 4: 5-((1R,3aR,6S,7R,7aS)-5,5-difluoro-7-((E)-2-(5-(3-fluorophenyl)pyridin-2-yl)vinyl)-1,6-dimethyl-3-oxooctahydroisobenzofuran-3a-yl)-1,3,4-oxadiazol-2(3H)-one: To a mixture of 5-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)-1,3,4-oxadiazol-2(3H)-one (51.7 mg, 0.11 mmol), (3-fluorophenyl)boronic acid (23.09 mg, 0.165 mmol) and tribasic potassium phosphate (0.165 mL, 0.330 mmol, 2 M in water) in THF (0.7 mL) was added 1,1'-bis(di-tert-butylphosphino)ferrocene palladium dichloride (3.58 mg, 5.50 μmol) at RT. The system was purged and flushed with $N_{2(g)}$ and the reaction mixture was stirred at 50° C. for 2 hours. The reaction mixture was diluted with EtOAc, and the organic was washed with water and brine. The organic phase was dried with $Na_2SO_4$, and was concentrated under reduced pressure. The crude was purified by silica gel chromatography (0-25% EtOAc in hexanes) to provide the title compound. MS ESI calcd. for $C_{25}H_{23}F_3N_3O_4$ [M+H]$^+$ 486, found 486. $^1$H NMR (500 MHz, CDCl$_3$) δ 8.81 (s, 1 H); 8.08 (d, J=8.3 Hz, 1 H); 7.59 (dd, J=7.95, 3.05 Hz, 1 H); 7.49-7.54 (m, 2 H); 7.47 (d, J=10.2 Hz, 1 H); 7.12-7.21 (m, 1 H); 6.75-6.78 (m, 2 H); 5.11-5.19 (m, 1 H); 3.08 (s, 1 H); 2.88 (m, 2 H); 2.37-2.59 (m, 2 H); 1.53 (dd, J=6.1, 3.0 Hz, 3 H); 1.05 (dd, J=6.8, 3.0 Hz, 3 H). PAR-1 FLIPR IC$_{50}$=28.7 nM.

Example 9

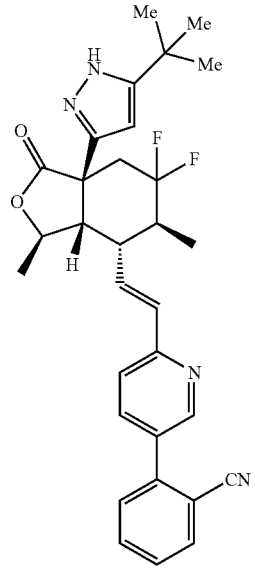 [SMILES: C[C@H]1OC(=O)[C@]2(c3cc(C(C)(C)C)[nH]n3)CC(F)(F)[C@@H](C)[C@H](/C=C/c3ccc(-c4ccccc4C#N)cn3)[C@H]12]

Step 1: (3R,3aS,4R,5S,7aR)-4-((E)-2-(5-bromopyridin-2-yl)vinyl)-6,6-difluoro-7a-((R)-1-hydroxy-4,4-dimethylpent-2-yn-1-yl)-3,5-dimethylhydroisobenzofuran-1(3H)-one: To (3R,3aS,4R,5S,7aR)-4-((E)-2-(5-bromopyridin-2-yl)vinyl)-6,6-difluoro-3,5-dimethylhexahydroisobenzofuran-1(3H)-one (600 mg, 1.55 mmol) in 2-Me- THF (6 mL) at 0° C. under N₂(g) was added lithium bis(trimethylsilyl)amide (325 mg, 1.94 mmol). The reaction mixture was stirred at 0° C. for 30 min before cooling the system to −78° C. and adding 4,4-dimethylpent-2-ynal (222 mg, 2.02 mmol). After stirring for 30 min at −78° C., the reaction mixture was allowed to warmed to RT and was stirred for 30 min. The reaction mixture was cooled to 0° C., quenched with saturated $NH_4Cl_{(aq)}$, and the product was extracted with EtOAc. The organic phase was washed with brine, dried with $Na_2SO_4$, and was concentrated. The residue was purified by column chromatography on silica (0-20% EtOAc in hexanes) to afford the title compound. MS ESI calcd. for $C_{24}H_{29}BrF_2NO_3$ [M+H]⁺ 496/498, found 496/498.

Step 2: (3R,3aS,4R,5S,7aR)-4-((E)-2-(5-bromopyridin-2-yl)vinyl)-7a-(4,4-dimethylpent-2-ynoyl)-6,6-difluoro-3,5-dimethylhexahydroisobenzofuran-1(3H)-one: To a solution of (3R,3aS,4R,5S,7aR)-4-((E)-2-(5-bromopyridin-2-yl)vinyl)-6,6-difluoro-7a-(1-hydroxy-4,4-dimethylpent-2-yn-1-yl)-3,5-dimethylhexahydroisobenzofuran-1(3H)-one (153 mg, 0.308 mmol) in DCM (1 mL) was added sodium bicarbonate (38.8 mg, 0.462 mmol) and Dess-Martin Periodinane (327 mg, 0.771 mmol) at RT. After 2 hours, the solvent was removed under reduced pressure and the residue was directly purified by silica gel chromatography (0-20% EtOAc in hexanes) to provide the title compound. MS ESI calcd. for $C_{24}H_{27}BrF_2NO_3$ [M+H]⁺ 494/496, found 494/496.

Step 3: (3R,3aS,4R,5S,7aR)-4-((E)-2-(5-bromopyridin-2-yl)vinyl)-7a-(5-(tert-butyl)-1H-pyrazol-3-yl)-6,6-difluoro-3,5-dimethylhexahydroisobenzofuran-1(3H)-one: To a solution of (3R,3aS,4R,5S,7aR)-4-((E)-2-(5-bromopyridin-2-yl)vinyl)-7a-(4,4-dimethylpent-2-ynoyl)-6,6-difluoro-3,5-dimethylhexahydroisobenzofuran-1(3H)-one (150 mg, 0.303 mmol) in EtOH (0.9 mL) was added hydrazine (0.029 mL, 0.910 mmol) at RT. After 30 min., the solvent was removed under reduced pressure and the crude residue was purified by silica gel chromatography (0-30% EtOAc in hexanes) to provide the title compound. MS ESI calcd. for $C_{24}H_{29}BrF_2N_3O_2$ [M+H]⁺ 508/510, found 508/510.

Step 4: 2-(6-((E)-2-((3R,3aS,4R,5S,7aR)-7a-(5-(tert-butyl)-1H-pyrazol-3-yl)-6,6-difluoro-3,5-dimethyl-1-oxooctahydroisobenzofuran-4-yl)vinyl)pyridin-3-yl)benzonitrile: To a mixture (3R,3aS,4R,5S,7aR)-4-((E)-2-(5-bromopyridin-2-yl)vinyl)-7a-(5-(tert-butyl)-1H-pyrazol-3-yl)-6,6-difluoro-3,5-dimethylhexahydroisobenzofuran-1(3H)-one (80 mg, 0.16 mmol), (2-cyanophenyl)boronic acid (34.7 mg, 0.236 mmol) and tribasic potassium phosphate (0.236 mL, 0.472 mmol, 2 M in water) in THF (1.0 mL) was added 1,1'-bis(di-tert-butylphosphino)ferrocene palladium dichloride (5.13 mg, 7.87 µmol) at RT. The system was purged and flushed with $N_{2(g)}$ and the reaction mixture was stirred at 50° C. for 4 hours. The reaction mixture was diluted with EtOAc, and the organic was washed with water and brine. The organic phase was dried with $Na_2SO_4$, and was concentrated under reduced pressure. The crude was purified by silica gel chromatography (0-45% EtOAc in hexanes) to provide the title compound. MS ESI calcd. for $C_{31}H_{33}F_2N_4O_2$ [M+H]⁺ 531, found 531. ¹H NMR (500 MHz, CDCl₃) δ 9.77-9.57 (br s, 1 H); 8.76 (d, J=2.3 Hz, 1 H); 7.95 (dd, J=8.1, 2.4 Hz, 1 H); 7.85 (d, J=7.7 Hz, 1 H); 7.74 (t, J=7.7 Hz, 1 H); 7.54-7.58 (m, 2 H); 7.35 (d, J=8.1 Hz, 1H); 6.76 (d, J=4.7 Hz, 2 H); 6.33 (s, 1H); 4.85 (dd, J=10.4, 5.8 Hz, 1 H); 3.22-3.32 (m, 1 H); 3.02-3.11 (m, 1 H); 2.81-2.93 (m, 1H); 2.18-2.33 (m, 2 H); 1.59 (d, J=12, 3 H); 1.39 (s, 9 H); 1.09 (d, J=6.6 Hz, 3 H). PAR-1 FLIPR $IC_{50}$=14.5 nM.

The following examples in Table 5 were prepared according to Schemes 3 and 4 using the procedure outlined in the synthesis of Example 9 using 4,4-dimethylpent-2-ynal, but-2-ynal, or 3-trimethylsilylpropynal in step 1 and known or commercially available boronic acids and esters in step 4.

TABLE 5

| Ex | Structure | IUPAC Name | Exact Mass [M + H]+ | PAR-1 FLIPR $IC_{50}$ (nM) |
|---|---|---|---|---|
| 10 | 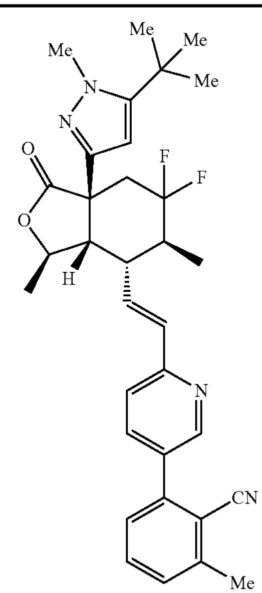 | 2-(6-((E)-2-((3R,3aS,4R,5S,7aR)-7a-(5-(tert-butyl)-1-methyl-1H-pyrazol-3-yl)-6,6-difluoro-3,5-dimethyl-1-oxooctahydroisobenzofuran-4-yl)vinyl)pyridin-3-yl)benzonitrile | 545 | 25.3 |

TABLE 5-continued

| Ex | Structure | IUPAC Name | Exact Mass [M + H]+ | PAR-1 FLIPR IC$_{50}$ (nM) |
|---|---|---|---|---|
| 11 | 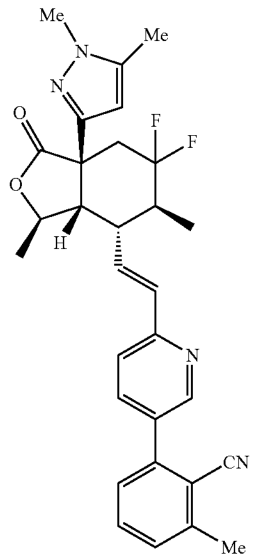 [SMILES: Cc1cccc(-c2ccc(/C=C/[C@@H]3[C@@H]4[C@@H](C)OC(=O)[C@]4(c4cc(C)n(C)n4)CC(F)(F)[C@H]3C)nc2)c1C#N] | 2-(6-((E)-2-((3R,3aS,4R,5S,7aR)-7a-(1,5-dimethyl-1H-pyrazol-3-yl)-6,6-difluoro-3,5-dimethyl-1-oxooctahydroisobenzofuran-4-yl)vinyl)pyridin-3-yl)benzonitrile | 517 | 6.30 |
| 12 | 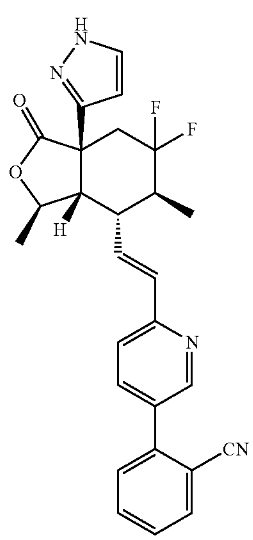 [SMILES: C[C@H]1OC(=O)[C@]2(c3cc[nH]n3)CC(F)(F)[C@@H](C)[C@H](/C=C/c3ccc(-c4ccccc4C#N)cn3)[C@H]12] | 2-(6-((E)-2-((3R,3aS,4R,5S,7aR)-6,6-difluoro-3,5-dimethyl-1-oxo-7a-(1H-pyrazol-3-yl)octahydroisobenzofuran-4-yl)vinyl)pyridin-3-yl)benzonitrile | 475 | 0.99 |

Example 13

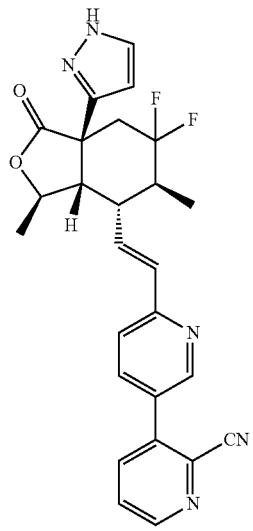 [SMILES: C[C@H]1OC(=O)[C@]2(c3cc[nH]n3)CC(F)(F)[C@@H](C)[C@H](/C=C/c3ccc(-c4cccnc4C#N)cn3)[C@H]12]

Step 1: 6'-((E)-2-((3R,3aS,4R,5S,7aR)-6,6-difluoro-7a-((S and R)-1-hydroxy-3-(trimethylsilyl)prop-2-yn-1-yl)-3,5-dimethyl-1-oxooctahydroisobenzofuran-4-yl)vinyl)-[3,3'-bipyridine]-2-carbonitrile: A solution of 6'-((E)-2-((3R,3aS,4R,5S,7aR)-6,6-difluoro-3,5-dimethyl-1-oxooctahydroisobenzofuran-4-yl)vinyl)-[3,3'-bipyridine]-2-carbonitrile (102 mg, 0.25 mmol) was dissolved in THF (2 mL). The solution was cooled to −78° C. and degassed by bubbling in nitrogen for 20 minutes followed by vacuum purging and flushing with nitrogen (3×). LiHMDS (1.0 M in THF, 325 μL, 0.325 mmol) was added and after 10 minutes, 3-trimethylsilylpropynal (51.7 μL, 0.350 mmol) was added. After 20 minutes at −78° C., the system was warmed to room temperature for an hour. The reaction was quenched with saturated aqueous NH$_4$Cl, then diluted with ethyl acetate and partitioned. The organic layer was washed with water, then with brine, dried over anhydrous sodium sulfate, filtered and concentrated. The residue was purified by chromatography (15-45% EtOAc/hexanes) to yield the title compound. MS ESI calcd. for $C_{29}H_{32}F_2N_3O_3Si$ [M+H]$^+$ 536, found 536.

Step 2: 6'-((E)-2-43R,3aS,4R,5S,7aR)-6,6-difluoro-3,5-dimethyl-1-oxo-7a-(3-trimethylsilyl) propioloyl)octahydroisobenzofuran-4-yl)vinyl)-[3,3'-bipyridine]-2-carbonitrile: To a solution of 6'-((E)-2-((3R,3aS,4R,5S,7aR)-6,6-difluoro-7a-((S and R)-1-hydroxy-3-(trimethyl silyl) prop-2-yn-1-yl)-3,5-dimethyl-1-oxooctahydroisobenzofuran-4-yl)vinyl)-[3,3'-bipyridine]-2-carbonitrile (94 mg, 0.175 mmol) in DCM (877 μL) was added Dess-Martin periodinane (112 mg, 0.263 mmol) at 0° C. After 90 min, the reaction was quenched with saturated aqueous NaHCO$_3$, diluted with DCM and partitioned. The organic was washed with saturated aqueous NaHCO$_3$ again, then dried over anhydrous sodium sulfate, filtered and evaporated. The residue was purified by silica chromatography (15-60% EtOAc/hexanes) to yield the title compound. MS ESI calcd. for $C_{29}H_{30}F_2N_3O_3Si$ [M+H]$^+$ 534, found 534.

Step 3: 6'-((E)-2-((3R,3aS,4R,5S,7aR)-6,6-difluoro-3,5-dimethyl-1-oxo-7a-(1H-pyrazol-3-yl)octahydroisobenzofuran-4-yl)vinyl)-[3,3'-bipyridine]-2-carbonitrile: To a solution of 6'-((E)-2-((3R,3aS,4R,5S,7aR)-6,6-difluoro-3,5-dimethyl-1-oxo-7a-(3-(trimethylsilyl)propioloyl) octahydroisobenzofuran-4-yl)vinyl)-[3,3'-bipyridine]-2-carbonitrile (80.5 mg, 0.151 mmol) in ethanol (1 mL) was added hydrazine (14.2 μL) at rt. After 45 minutes, the reaction was partitioned between water and ethyl acetate. The organic was water and then with brine, dried over anhydrous sodium sulfate, filtered and evaporated. The residue was purified by silica chromatography (20-100% EtOAc/hexanes) and to yield the title compound. MS ESI calcd. for $C_{26}H_{24}F_2N_5O_2$ [M+H]$^+$ 476, found 476. $^1$H NMR (500 MHz, CDCl$_3$) δ 8.76 (dd, 1H, J=4.7 Hz, 1.3 Hz), 8.73 (d, 1H, J=2.2 Hz), 7.95 (dd, 1H, J=8.0 Hz, 2.3 Hz), 7.89 (dd, 1H, J=8.0 Hz, 1.3 Hz), 7.64 (m, 2H), 7.36 (d, 1H, J=8.2 Hz), 6.75 (m, 2H), 6.59 (d, 1H, J=2.4 Hz), 4.85 (m, 1H), 3.24 (m, 1H), 3.02 (m, 1H), 2.87 (m, 1H), 2.32-2.14 (m, 2H), 1.57 (d, 3H, J=5.8 Hz), 1.05 (d, 3H, J=6.6 Hz). PAR-1 FLIPR IC$_{50}$=6.2 nM L-005346192.

Assays

The following assays were used to evaluate the ability of the inventive compounds to act as PAR-1 receptor antagonists and their interactions with other therapeutic agents in the body.

PAR-1 FLIPR Assay

This assay measures the potency of the inventive compounds as PAR-1 receptor antagonists.

Frozen HEK 293 Cells were plated in 384-well PDL coated plates at 12000 cells/well in 50 uL of DMEM media containing 10% FBS, pen/strep/L-Glutamine and non-essential amino acids, incubated overnight at 37° C./5% CO$_2$. Media was then removed from the cells, incubated with 33 uL of Calcium-5 dye in assay buffer (Hank's buffer containing 20 mM HEPES, 0.04% Chaps and 2.5 mM Probenecid) for 60 minutes at 37° C. 2 uL of varying concentrations of compound in 40% DMSO in assay buffer (final DMSO concentration is 2.3%) were then added to the cells and incubated at 25° C. for 30 minutes. The plates were added to the FLIPR Tetra®, the device added 5 μL of PAR-1 selective receptor-activating peptide (sequence Ala-para-fluoroPhe-Arg-Cha-Cit-Try-NH$_2$, prepared in water) at a concentration equal to the effective concentration that achieved 80% activation of signaling on the day of the experiment. The range of peptide was from 1.5-3 μM. The final volume is 40 uL/well, with 2% DMSO. The FLIPR was read at an excitation wavelength of 480 nm and an emission wavelength of 535 nm, and performed 60 scans over a 1-2 min reading time. The data were analyzed by taking the peak signal over a portion of the range of the 60 scans and dividing this signal by the minimum signal for that same range. The data were expressed as percent inhibition of the maximum divided by the minimum signal achieved at 80% activation produced by the PAR1 activating peptide on the test day. The compounds of Examples 1-13 were tested in the assay described above and the data collected for these compounds is provided.

CYP MUX (3A4) RI

This assay measures inhibition of CYP3A4 by a compound. Cytochromes P450 (CYPs) constitute a superfamily of heme-containing enzymes that recognize and metabolize a large number structurally diverse xenobiotics in the human body. CYP3A4 constitutes the largest portion of CYP enzymes in the liver that accounts for the metabolism of almost 50% of all drugs. This assay is used to evaluate the potential of a compound for developing DDIs. (Clarke, S. E.; Jones B. C. *Drug-Drug Interactions*, New York: Marcel Dekker; 2002. pp. 53-88).

Compound dilutions and assay-ready plates were prepared on a TTP Labtech mosquito® HTS. Assay conduction was fully automated on a customized Screening Platform from Caliper (now PerkinElmer) containing a Mitsubishi robotic plate handler, Liconic incubators, a Caliper Zephyr® liquid handling workstation equipped with temperature-controlled deck positions, a Biotek MultiFlo™ dispenser and an Agilent PlateLoc heat sealer. Assay plates were Corning Costar® 384 well PP plates. High throughput mass spectrometric readout was performed on a RapidFire® 300 system coupled to an AB Sciex API 4000™ triple quadrupole device. CYP isoform 3A4 was incubated in a separate reaction of 50 µL final volume. 25 µL of HLM (human liver microsomes, BD UltraPool™ 150, 0.25 mg/mL final concentration) and the respective substrate, testosterone (75 µM) for 3A4, in potassium phosphate buffer (100 mM, pH=7.4) were added to 250 nL of stamped compound solution (10 mM in DMSO). The reactions were started upon addition of 25 µL of a co-factor solution containing magnesium chloride (3.3 mM), glucose-6-phosphate (3.3 mM), glucose-6-phosphate dehydrogenase (1.4 units) and NADP (1 mM) in potassium phosphate buffer (100 mM, pH=7.4) and incubated on deck at 37° C. for 10 min. 8 µL of each reaction were transferred to the same readout plated filled with 48 µL of stop solution containing internal standards (concentration in final readout plate), 6-hydroxytestosterone-D7 (0.5 µM), 4'-hydroxydiclofenac-D4 (0.2 and dextrorphan-D3 (0.01 in acetonitrile with 0.5% formic acid. After heat sealing, plates were stored at −20° C. for at least 30 min, centrifuged and subjected directly to RapidFire®/MS analysis.

The selectivity of the inventive compounds in CPY3A4 assay is summarized in Table 6 below.

TABLE 6

| Ex | CYP3A4 IC$_{50}$ (µM) |
|---|---|
| 1 | 21.8 |
| 2 | 22.8 |
| 3 | 10.4 |
| 4 | 9.9 |
| 5 | 16.9 |
| 6 | 50 |
| 7 | 50 |
| 8 | 50 |
| 9 | 50 |
| 10 | 50 |
| 11 | 17.6 |
| 12 | 2.4 |
| 13 | 8.8 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereo configuration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

The invention claimed is:

1. A compound of the formula

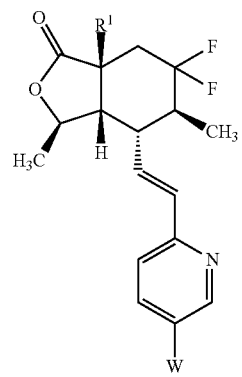

or a pharmaceutically acceptable salt thereof
wherein:
  $R^1$ is

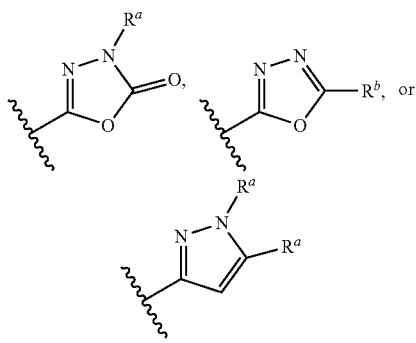

W is

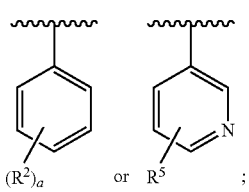

each $R^a$ is independently H or $C_1$-$C_4$ alkyl;
$R^b$ is H; $C_1$-$C_4$ alkyl; cycloalkyl; —N($R^3$)($R^4$); or phenyl, which is optionally substituted once or twice by alkyl, haloalkyl, —OH, or alkoxy;
each $R^2$ is independently halo; —CN; alkyl; or haloalkyl;
$R^3$ is H or alkyl;
$R^4$ is H or alkyl;
$R^5$ is H, alkyl or —CN; and
a is 0, 1 or 2.

2. The compound of claim 1 or a pharmaceutically acceptable salt thereof wherein W is

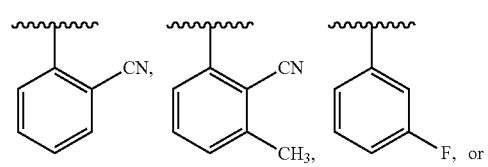

-continued

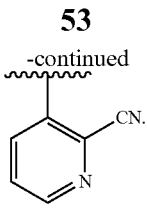

3. A compound of claim 1 which is:
2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl)benzonitrile;
2-(6-((E)-2-((3R,3aS,4R,5S,7aR)-6,6-difluoro-3,5-dimethyl-1-oxo-7a-(5-oxo-4,5-dihydro-1,3,4-oxadiazol-2-yl)octahydroisobenzofuran-4-yl)vinyl)pyridin-3-yl)-6-methylbenzonitrile;
2-(6-((E)-2-((3R,3aS,4R,5S,7aR)-7a-(5-amino-1,3,4-oxadiazol-2-yl)-6,6-difluoro-3,5-dimethyl-1-oxooctahydroiso benzofuran-4-yl)vinyl)pyridin-3-yl)-6-methylbenzonitrile;
2-(6-((E)-2-((3R,3aS,4R,5S,7aR)-7a-(5-amino-1,3,4-oxadiazol-2-yl)-6,6-difluoro-3,5-dimethyl-1-oxooctahydroiso benzofuran-4-yl)vinyl)pyridin-3-yl) benzonitrile;
2-(6-((E)-2-((3R,3aS,4R,5S,7aR)-6,6-difluoro-3,5-dimethyl-7a-(5-methyl-1,3,4-oxadiazol-2-yl)-1-oxooctahydroisobenzofuran-4-yl)vinyl)pyridin-3-yl)-6-methylbenzonitrile;
2-(6-((E)-2-((3R,3aS,4R,5S,7aR)-7a-(5-cyclopropyl-1,3,4-oxadiazol-2-yl)-6,6-difluoro-3,5-dimethyl-1-oxooctahydroisobenzofuran-4-yl)vinyl) pyridin-3-yl)-6-methylbenzonitrile;
2-(6-((E)-2-((3R,3aS,4R,5S,7aR)-6,6-difluoro-3,5-dimethyl-1-oxo-7a-(5phenyl -1,3,4-oxadiazol-2-yl) octahydroisobenzofuran-4-yl)vinyl)pyridin-3-yl)-6-ethylbenzonitrile;
5-((1R,3aR,6S,7R,7aS)-5,5-difluoro-7-((E)-2-(5-(3-fluorophenyl)pyridin-2-yl)vinyl)-1,6-dimethyl-3-oxooctahydroisobenzofuran-3a-yl)-1,3,4-oxadiazol-2(3H)-one;
2-(6-((E)-2-((3R,3aS,4R,5S,7aR)-7a-(5-(tert-butyl)-1H-pyrazol-3-yl)-6,6-difluoro-3,5-dimethyl-1-oxooctahydroisobenzofuran-4-yl)vinyl)pyridin-3-yl) benzonitrile;
2-(6-((E)-2-((3R,3aS,4R,5S,7aR)-7a-(5-(tert-butyl)- 1 -methyl- 1H-pyrazol-3-yl)-6,6-difluoro-3,5-dimethyl-1-oxooctahydroisobenzofuran-4-yl)vinyl) pyridin-3-yl)benzonitrile;

2-(6-((E)-2-((3R,3aS,4R,5S,7aR)-7a-(1,5-dimethyl-1H-pyrazol-3-yl)-6,6-difluoro-3,5-dimethyl-1-oxooctahydroiso benzofuran-4-yl)vinyl)pyridin-3-yl)benzonitrile;
2-(6-((E)-2-((3R,3aS,4R,5S,7aR)-6,6-difluoro-3,5-dimethyl-1-oxo-7a-(1H-pyrazol-3-yl)octa hydroisobenzofuran- 4-yl)vinyl)pyridin-3-yl)benzonitrile;
6'-((E)-2-((3R,3aS,4R,5S,7aR)-6,6-difluoro-3,5-dimethyl-1-oxo-7a-(1H-pyrazol-3-yl)octahydroisobenzofuran-4-yl)vinyl)-[3,3'-bipyridine]-2-carbonitrile;
or a pharmaceutically acceptable salt thereof.

4. A pharmaceutical composition comprising an effective amount of a compound as defined in claim 1 or a pharmaceutically acceptable salt thereof and a pharmaceutically acceptable carrier.

5. The pharmaceutical composition as defined in claim 4, which further comprises a therapeutically effective amount of at least one additional cardiovascular agent.

6. The pharmaceutical composition as defined in claim 5, wherein the at least one additional cardiovascular agent is aspirin or clopidogrel, wherein clopidogrel is a free base or pharmaceutically acceptable salt.

7. A pharmaceutical composition comprising an effective amount of a compound as defined in claim 3 or a pharmaceutically acceptable salt thereof and a pharmaceutically acceptable carrier.

8. The pharmaceutical composition as defined in claim 7, which further comprises a therapeutically effective amount of at least one additional cardiovascular agent.

9. The pharmaceutical composition as defined in claim 8, wherein the at least one additional cardiovascular agent is aspirin or clopidogrel, wherein clopidogrel is a free base or pharmaceutically acceptable salt.

10. A method for treating acute coronary syndrome or peripheral artery disease by administering a compound as defined in claim 1
or a pharmaceutically acceptable salt thereof
to a mammal in need of such treatment.

11. A method of inhibiting platelet aggregation comprising administering to a mammal an effective amount of a compound as defined in claim 1 or a pharmaceutically acceptable salt thereof.

12. A method for treating acute coronary syndrome or peripheral artery disease by administering a compound as defined in claim 3
or a pharmaceutically acceptable salt thereof to a mammal in need of such treatment.

13. A method of inhibiting platelet aggregation comprising administering to a mammal an effective amount of a compound as defined in claim 3
or a pharmaceutically acceptable salt thereof.

* * * * *